United States Patent
Tague et al.

(10) Patent No.: US 7,645,066 B2
(45) Date of Patent: Jan. 12, 2010

(54) METHOD OF MIXING BONE CEMENT WITH TWO MIXING PADDLES

(75) Inventors: Christopher Matthew Tague, Portage, MI (US); Richard F. Huyser, Kalamazoo, MI (US); Jared Paul Coffeen, Paw Paw, MI (US); Christopher Scott Brockman, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 327 days.

(21) Appl. No.: 11/301,177

(22) Filed: Dec. 12, 2005

(65) Prior Publication Data

US 2006/0087912 A1 Apr. 27, 2006

Related U.S. Application Data

(62) Division of application No. 10/388,015, filed on Mar. 13, 2003, now Pat. No. 6,994,465.

(60) Provisional application No. 60/364,171, filed on Mar. 14, 2002.

(51) Int. Cl.
  *B01F 7/20* (2006.01)
  *B01F 13/06* (2006.01)
(52) U.S. Cl. .................................. 366/245; 366/139
(58) Field of Classification Search .................. 366/139, 366/242–246
  See application file for complete search history.

(56) References Cited

U.S. PATENT DOCUMENTS

| 92,738 A | 7/1869 | Mitchell |
|---|---|---|
| 356,694 A | 1/1887 | Morey |
| 514,358 A | 2/1894 | Grant |
| 795,082 A | 7/1905 | Warner |
| 818,914 A | 4/1906 | Perrin |
| 846,872 A | 3/1907 | Stewart |
| 849,273 A | 4/1907 | Schuirmann et al. |
| 929,900 A | 8/1909 | Torbett |
| 1,002,931 A | 9/1911 | Reaume |
| 1,138,815 A | 5/1915 | Voss |
| 1,180,020 A | 4/1916 | Dilg |
| 1,612,281 A | 12/1926 | Goetz |
| 2,184,225 A | 12/1939 | McDuffee et al. |

(Continued)

FOREIGN PATENT DOCUMENTS

CA 558762 6/1958

(Continued)

OTHER PUBLICATIONS

Supplementary Partial European Search Report dated Sep. 4, 2006 for EP Application No. 03744651.

*Primary Examiner*—David L Sorkin
(74) *Attorney, Agent, or Firm*—Howard & Howard Attorneys PLLC

(57) ABSTRACT

A mixing assembly for mixing bone cement includes a housing, a lid, a handle, and two mixing paddles, a first and a second mixing paddle. The lid is removably attachable to the housing. The handle has a portion that extends through the lid and that is rotatable in a first rotational direction. The first mixing paddle is operatively coupled to the portion of the handle. As a result, the first mixing paddle rotates with the portion of the handle in the first rotational direction. The second mixing paddle is operatively coupled to the first mixing paddle for rotating opposite the portion. As such, when the portion of the handle and the first mixing paddle rotate in the first rotational direction, the second mixing paddle rotates in a second rotational direction that is opposite the first rotational direction.

20 Claims, 25 Drawing Sheets

U.S. PATENT DOCUMENTS

| | | |
|---|---|---|
| 2,203,135 A | 6/1940 | Farrington |
| 2,453,914 A | 11/1948 | Hollenback |
| 2,539,436 A | 1/1951 | Kost |
| 2,677,504 A * | 5/1954 | Klingel ................... 241/17 |
| 2,696,022 A | 12/1954 | Steinbock et al. |
| 3,006,614 A * | 10/1961 | Beach ..................... 366/139 |
| 3,126,196 A | 3/1964 | Staeger |
| 3,131,912 A | 5/1964 | Steinbock, Jr. |
| 3,358,971 A | 12/1967 | Steinbock, Jr. |
| 3,640,510 A | 2/1972 | Lea |
| 3,861,656 A | 1/1975 | Schmitt |
| 4,079,917 A | 3/1978 | Popell |
| 4,185,072 A | 1/1980 | Puderbaugh et al. |
| 4,277,184 A | 7/1981 | Solomon |
| 4,721,390 A | 1/1988 | Lidgren |
| 4,758,096 A | 7/1988 | Gunnarsson |
| 4,787,751 A | 11/1988 | Bakels |
| 4,854,716 A | 8/1989 | Ziemann et al. |
| 4,946,285 A | 8/1990 | Vennemeyer |
| 4,961,647 A | 10/1990 | Coutts et al. |
| 4,973,168 A | 11/1990 | Chan |
| 5,015,101 A | 5/1991 | Draenert |
| 5,044,761 A | 9/1991 | Yuhki et al. |
| 5,100,241 A | 3/1992 | Chan |
| 5,114,240 A | 5/1992 | Kindt-Larsen et al. |
| 5,145,250 A | 9/1992 | Planck et al. |
| 5,167,448 A | 12/1992 | Herold et al. |
| 5,193,907 A | 3/1993 | Faccioli et al. |
| 5,252,301 A | 10/1993 | Nilson et al. |
| 5,265,956 A | 11/1993 | Nelson et al. |
| 5,348,391 A | 9/1994 | Murray |
| 5,368,386 A | 11/1994 | Murray |
| 5,395,167 A | 3/1995 | Murray |
| 5,494,349 A | 2/1996 | Seddon |
| 5,505,538 A * | 4/1996 | Earle ..................... 366/139 |
| 5,556,201 A | 9/1996 | Veltrop et al. |
| D381,084 S | 7/1997 | Vish |
| 5,842,786 A * | 12/1998 | Solomon ................. 366/139 |
| 5,876,116 A | 3/1999 | Barker et al. |
| 5,934,803 A * | 8/1999 | Hutter ..................... 366/139 |
| 5,961,211 A | 10/1999 | Barker et al. |
| 5,975,751 A | 11/1999 | Earle |
| 6,033,105 A | 3/2000 | Barker et al. |
| 6,042,262 A | 3/2000 | Hajianpour |
| 6,120,174 A * | 9/2000 | Hoag et al. ............... 366/139 |
| 6,254,268 B1 | 7/2001 | Long |
| 6,599,005 B2 * | 7/2003 | Van Der Wel ............ 366/143 |
| 2002/0067658 A1 | 6/2002 | Vendrely et al. |
| 2003/0174576 A1 | 9/2003 | Tague et al. |

FOREIGN PATENT DOCUMENTS

| | | |
|---|---|---|
| DE | 3113141 | 8/1982 |
| EP | 0402668 | 12/1990 |
| FR | 1477824 | 4/1967 |
| FR | 2597321 | 10/1987 |
| GB | 178572 | 4/1922 |
| GB | 517340 | 1/1940 |
| GB | 1187140 | 4/1970 |
| JP | 449251 | 4/1969 |
| JP | 5712226 | 1/1982 |
| JP | 02058503 | 2/1990 |
| JP | 672539 | 10/1994 |
| JP | 1076151 | 3/1998 |
| WO | 9310892 | 6/1993 |

* cited by examiner

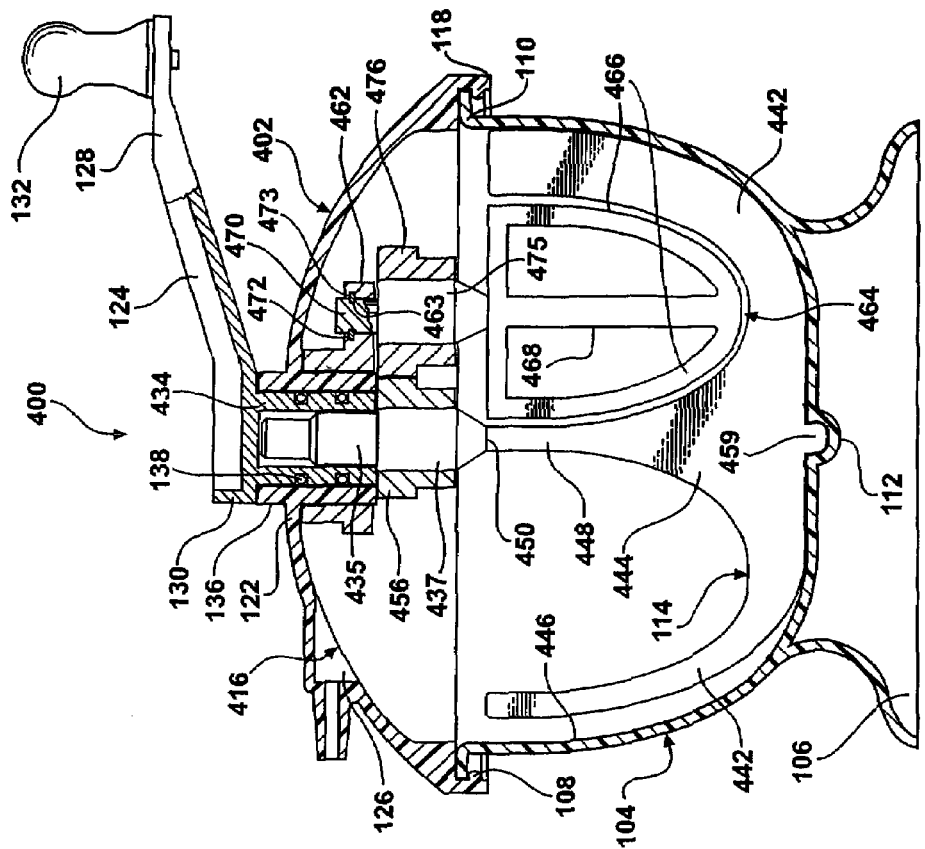
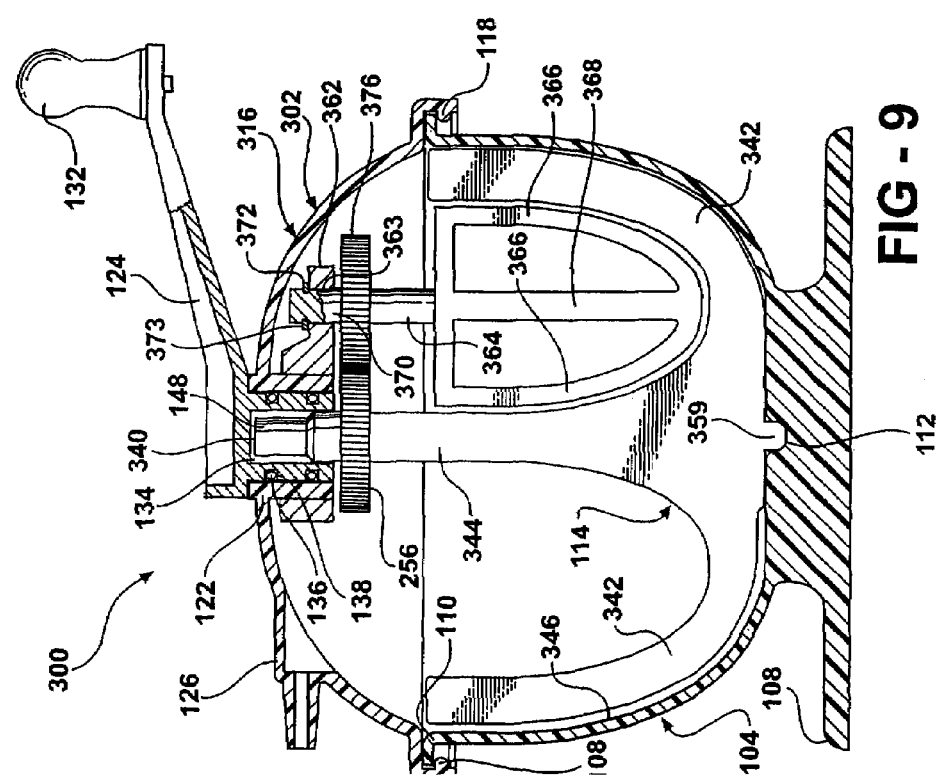

METHOD OF MIXING BONE CEMENT WITH TWO MIXING PADDLES

RELATED APPLICATIONS

This patent application is a divisional of application Ser. No. 10/388,015, filed Mar. 13, 2003 now U.S. Pat. No. 6,994,465, which claims priority to and all advantages of U.S. Provisional Patent Application No. 60/364,171, which was filed on Mar. 14, 2002, both of which are hereby incorporated by reference in their entirety.

BACKGROUND OF THE INVENTION

1. Field of the Invention

The subject invention generally relates to a mixing assembly for mixing bone cement.

2. Description of the Related Art

The application of bone cement to a bone during surgical procedures, such as the attachment of a prosthesis or pathological fracture fixation, is well known in the surgical community. With regard to the attachment of a prosthesis, the cement is packed into the bone and the prosthesis is then attached. The cement cures and a bond develops between the bone and the prosthesis. Other uses of bone cement include repairing or mending bone fractures or shattered bone occurring from extreme trauma. Bone cement may also be used during cosmetic or dental surgery. Moreover, bone cement may be used as a drug delivery or release system, whereby the bone cement is mixed with antibiotics or other desired drugs and applied to a specific surgical site such that the drugs leach out and are delivered directly to the surgical site. Some bone cements are also designed to be absorbed by the body over time.

Typically, the bone cement is prepared by thoroughly blending two components. Typical bone cement mixtures comprise a powdered polymer or copolymer, such as a polymethylmethacrylate, and a liquid monomer, usually a methylmethacrylate. Conventionally, the combining of the powder and liquid components is carried out using a container and a spatula resulting in the formation of a quick setting bone cement material. Because of its quick setting nature, the bone cement is usually prepared in the surgical room in conjunction with the surgical procedure. Once the bone cement is thoroughly mixed, the surgeon promptly removes the necessary amount of cement, inserts it into a delivery device or manipulates it by hand, and applies it to the appropriate surface or cavity before the cement mixture cures or hardens. However, there are a number of disadvantages to this method of mixing bone cement.

First, combining the monomer liquid and polymer powder causes noxious flumes to be emitted. Thus, it is desirable to prevent these fumes from escaping into the atmosphere. Second, the cement ingredients must be mixed quickly, thoroughly and uniformly to maximize homogeneity while reducing or eliminating the formation of air bubbles to impart high mechanical strength and bonding properties to the bone cement. Inherent in the mixing process, air bubbles are generated in the mixture from air residing in the powder and in the mixing container. Moreover, air bubbles are produced when the monomer vaporizes to produce a gas during the mixing process.

To evacuate the maximum amount of air and gas entrapped in the container and mixture, it is known in the art to perform the mixing in a mixing chamber under vacuum. Further, various devices are available wherein cement may be mixed under vacuum. Such devices include a mixing chamber coupled with a dispensing syringe connected to a vacuum source. Although such devices are efficient and clean, they are expensive and inhibit application of the cement compound by hand, which may be the preferred or necessary method in a given procedure.

Alternatively, mixing assemblies, i.e., cement mixing bowls, are also known in the art. Such mixing bowls generally include a housing and a lid defining a mixing chamber with a mixing paddle extending into the housing and disposed in the mixing chamber. Typically, the mixing paddle is rotated, i.e., driven by a handle extending out of the lid. In addition, the mixing chamber is generally connectable to a vacuum source for creating a vacuum within the mixing chamber.

Such mixing bowls are disclosed in U.S. Pat. Nos. 5,494,349 and 6,254,268. These mixing bowls are deficient for a variety of reasons. Overall, these mixing bowls do not provide adequate mixing and do not permit establishment of a sufficient hermetic seal. For example, the mixing bowl disclosed in the '349 patent to Seddon does not provide adequate mixing of the monomer liquid and polymer powder. More specifically, the single mixing paddle disclosed in the '349 patent, which only rotates in one direction, does not adequately mix the monomer liquid and the polymer powder. Ultimately, inadequate mixing of these two components results in a bone cement that lacks the required mechanical strength and bonding properties. The mixing bowl disclosed in the '349 patent is also deficient because the mixing paddle is not adequately biased against an interior wall of the housing, specifically a bottom interior wall, to sufficiently scrape the bone cement from the interior wall. As a result, excessive air and gas bubbles can remain present in the bone cement, which is detrimental to various properties of the cement. Instead, to have this mixing paddle adequately biased against the interior wall of the housing, the lid either cannot be tightened about the housing such that a completely hermetic seal is not established, or the lid has to be tightened too much about the housing such that the completeness of any hermetic seal is sacrificed. More specifically, the lid in the '349 is particularly susceptible to deflection when the mixing bowl is under vacuum. This deflection may 'pinch' the mixing paddle at the bottom interior wall such that increased torque is required to mix the bone cement. When the mixing bowl of the '349 patent is not under vacuum, there is typically a large gap between the mixing paddle and the interior wall of the housing. The mixing bowl of the '349 patent is further deficient in that it does not strategically incorporate a gear set that provides for more than one mixing paddle and for more than one rotational direction for optimum mixing of the bone cement. The mixing bowl disclosed in the '268 patent to Long realizes theses same deficiencies.

Due to the deficiencies associated with the mixing assemblies of the prior art, including those described above, it is desirable to provide a unique mixing assembly that solves one or more of these deficiencies.

SUMMARY OF THE INVENTION AND ADVANTAGES

A mixing assembly for mixing bone cement is disclosed. The mixing assembly includes a housing having an interior wall and a lid that is removably attachable to the housing. The mixing assembly also includes a handle and a first and second mixing paddle. The handle includes a portion that extends through the lid and that is rotatable in a first rotation direction. The first mixing paddle is operatively coupled to the portion of the handle for rotating with the portion of the handle in the first rotational direction. The second mixing paddle is operatively coupled to the first mixing paddle for rotating opposite the portion of the handle. As such, when the portion and the first mixing paddle rotate in the first rotational direction, the second mixing paddle rotates in a second rotational direction that is opposite the first rotational direction.

In a further embodiment of the subject invention, the lid of the mixing assembly, which is removably attachable to the housing, is movable between an open position and a sealed position. In the open position, the bone cement can be added to the housing, and in the sealed position, the lid is hermetically sealed to the housing to define a sealed mixing chamber between the lid and the interior wall of the housing for mixing the bone cement. This particular embodiment may only include one mixing paddle, specifically the first mixing paddle, is operatively coupled to the portion of the handle for rotating with the portion. The mixing paddle is movable between an extended position when the lid is in the open position and a retracted position. When the lid is in the sealed position and the mixing paddle is in the retracted position, the mixing paddle is adapted to scrape the bone cement from the interior wall when the lid is in the sealed position. A resilient member is disposed between the portion of the handle and the mixing paddle. The resilient member normally-biases the mixing paddle into the extended position. However, the resilient member also compresses in response to contact between the mixing paddle and the interior wall as the lid is moved from the open position to the sealed position. This compression permits the mixing paddle to retract into the retracted position such that the lid can be hermetically sealed to the housing in the sealed position. In this position, the mixing paddle can still scrape the bone cement from the interior wall.

In yet a further embodiment of the subject invention, the mixing assembly incorporates a gear set that is disposed between the first and second mixing paddles. The gear set operatively couples the second mixing paddle to the first mixing paddle such that the second mixing paddle rotates opposite the portion of the handle in the second rotational direction and about a second fixed axis or rotation when the portion and the first mixing paddle are rotating in the first rotational direction about a first fixed axis of rotation.

The primary advantage of the present invention is that the mixing assembly provides adequate mixing of a monomer liquid and polymer powder, which results in a bone cement that has sufficient mechanical strength and bonding properties. The first and second mixing paddles, and more specifically the opposite rotational directions respectively associated with the first and second mixing paddles, enable the adequate mixing. With adequate mixing, the bone cement is conducive to many different application techniques including application of the bone cement by hand. The mixing assembly of the subject invention also enables a complete hermetic seal to be established between the housing and the lid such that fumes and the monomer and polymer components do not escape from the sealed mixing chamber.

Further, the mixing paddle utilized in the mixing assembly of the subject invention is biased against the interior wall of the housing, by the resilient member, such that the mixing paddle can sufficiently scrape the bone cement from the interior wall. This further enhances mixing and eliminates excessive air and gas bubbles from the bone cement. Furthermore, by scraping the bone cement, the mixing paddle reduces the amount of any unmixed powder such that a more complete, homogeneous mix of the bone cement can be attained. Also, a complete, and lasting, hermetic seal is established with this mixing bowl as the lid is moved about the housing, even while the mixing paddle is biased against the interior wall of the housing.

BRIEF DESCRIPTION OF THE DRAWINGS

Other advantages of the present invention will be readily appreciated as the same becomes better understood by reference to the following detailed description when considered in connection with the accompanying drawings wherein:

FIG. 9 is a partially cross-sectional view of the mixing assembly according to another embodiment of the present invention;

FIG. 10 is a partially cross-sectional view of the mixing assembly according to another embodiment of the present invention;

DETAILED DESCRIPTION OF THE PREFERRED EMBODIMENT

Figure 23:
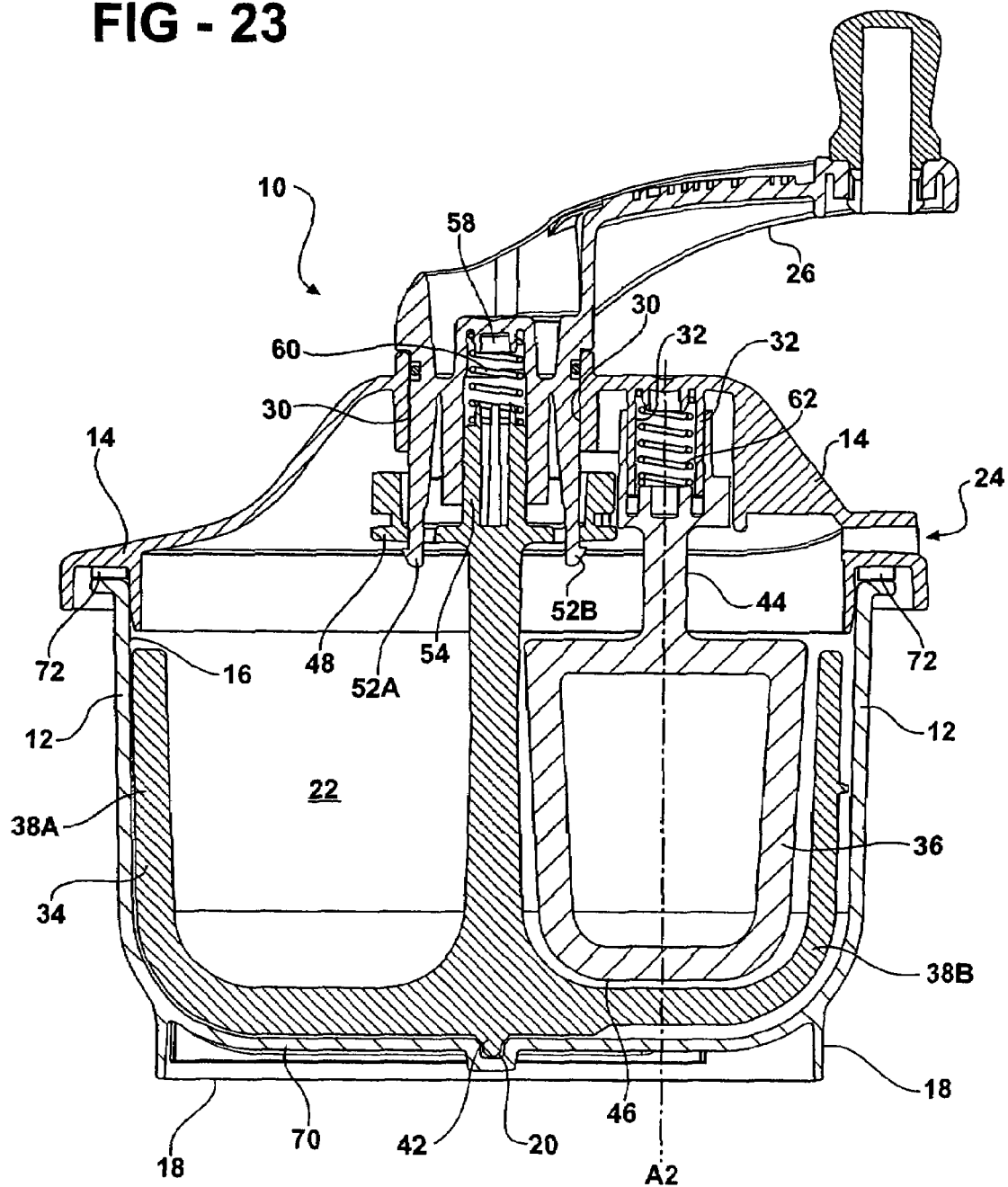
FIG. 23 is a cross-sectional view of the mixing assembly of FIG. 22.
Figure 24:
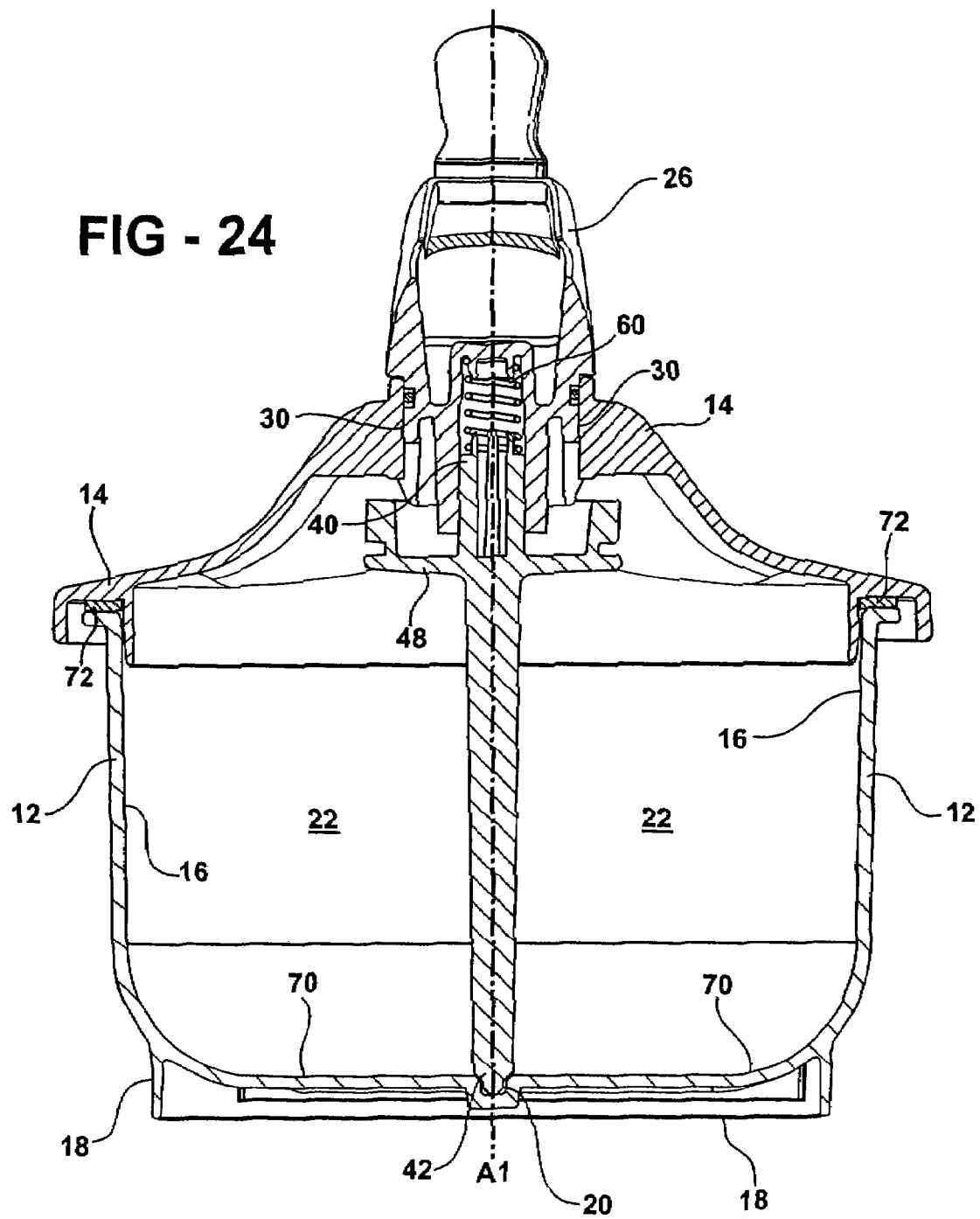
FIG. 24 is partially cross-sectional view of the mixing assembly of FIG. 22.
Figure 25:
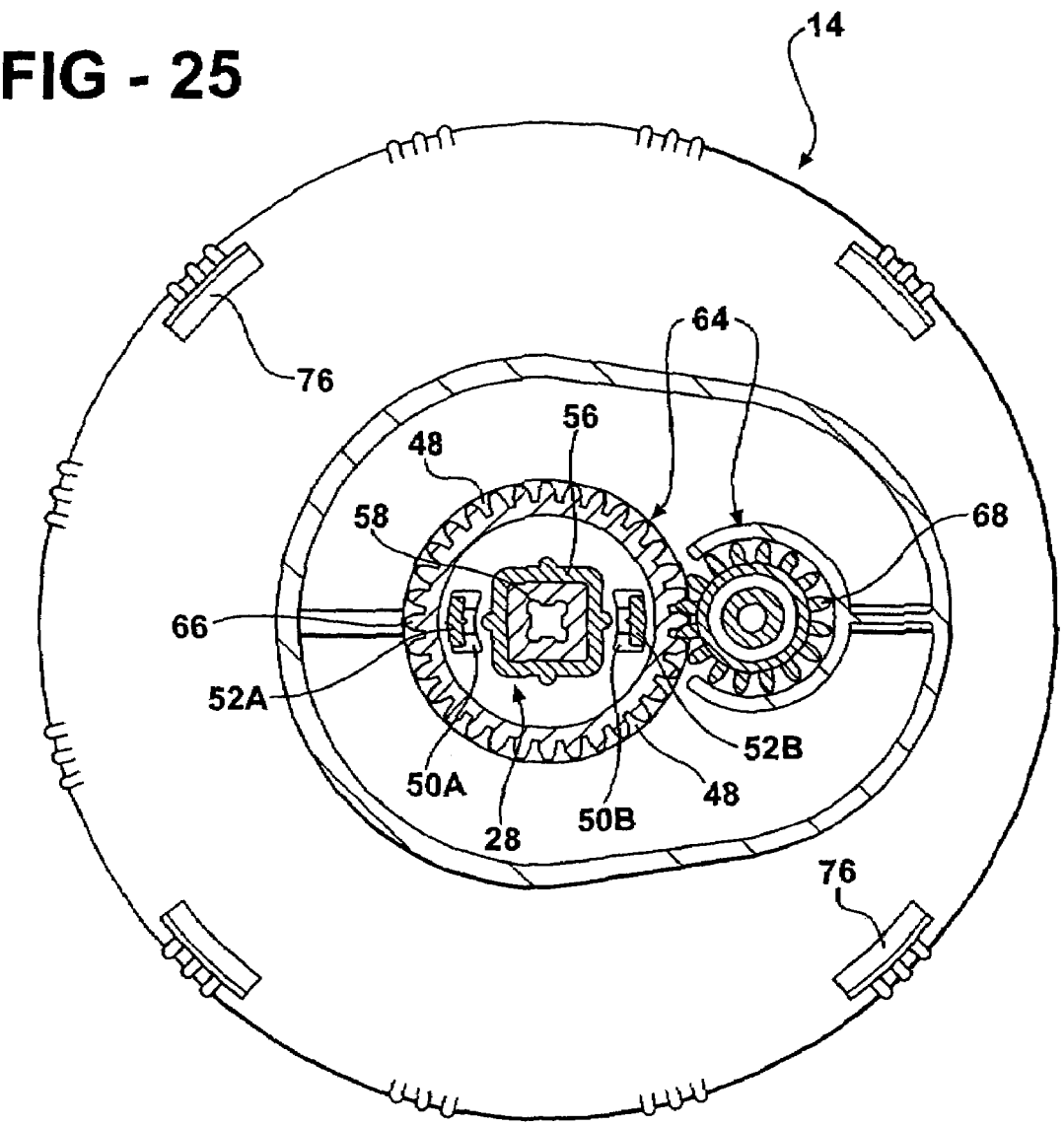
FIG. 25 is another cross-sectional view of the mixing assembly of FIG. 22.
Figure 26:
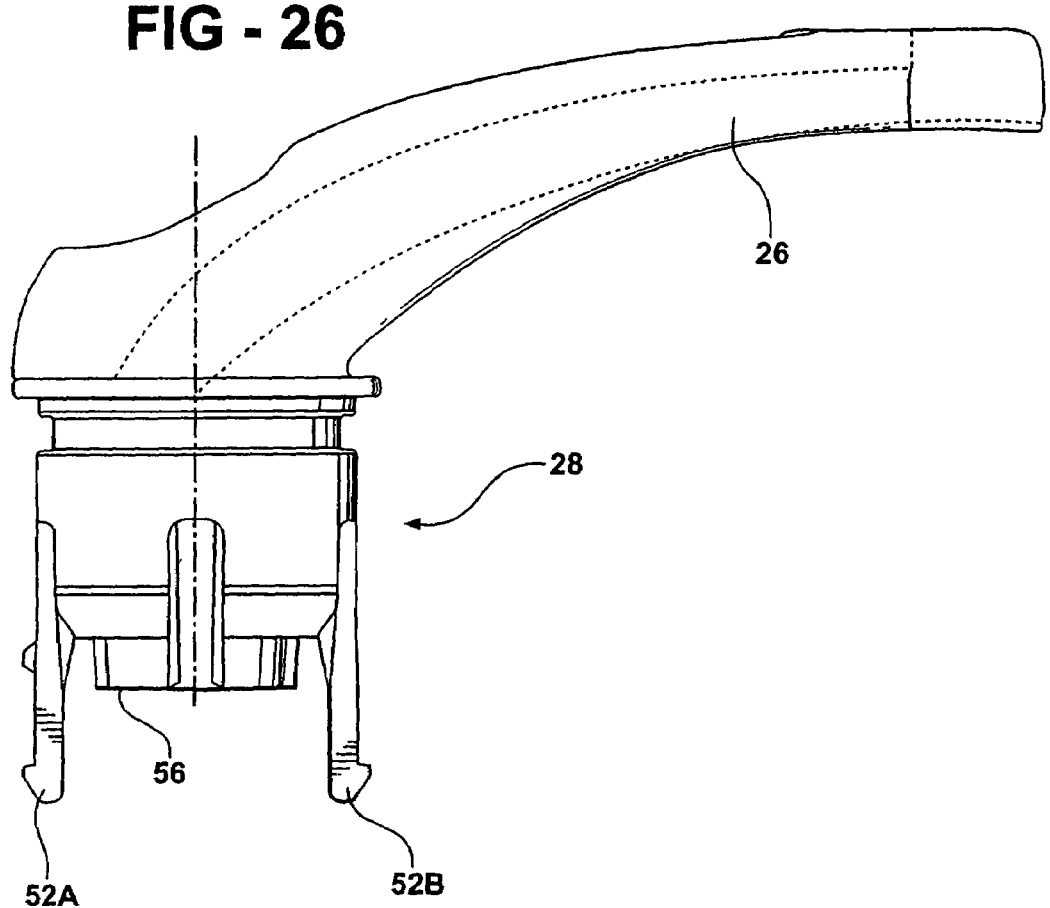
FIG. 26 is a view of the mixing assembly illustrating a portion of the handle and the handle.
Figure 27:
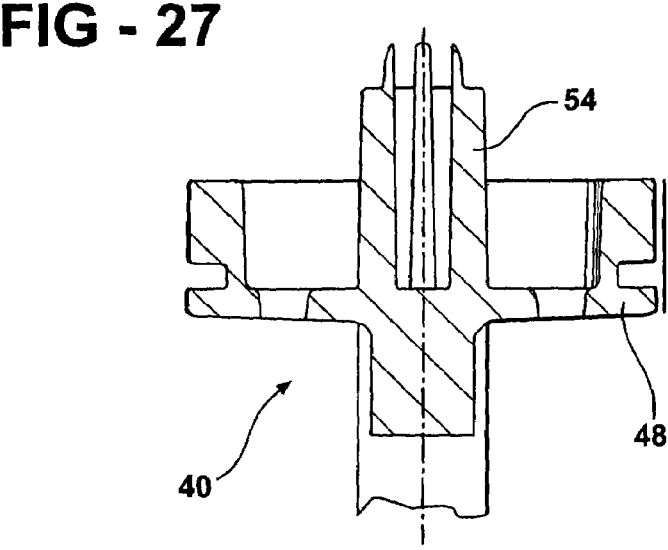
FIG. 27 is a cross-sectional view of a first end of the first mixing paddle for the mixing assembly of FIG. 22.
Figure 28:
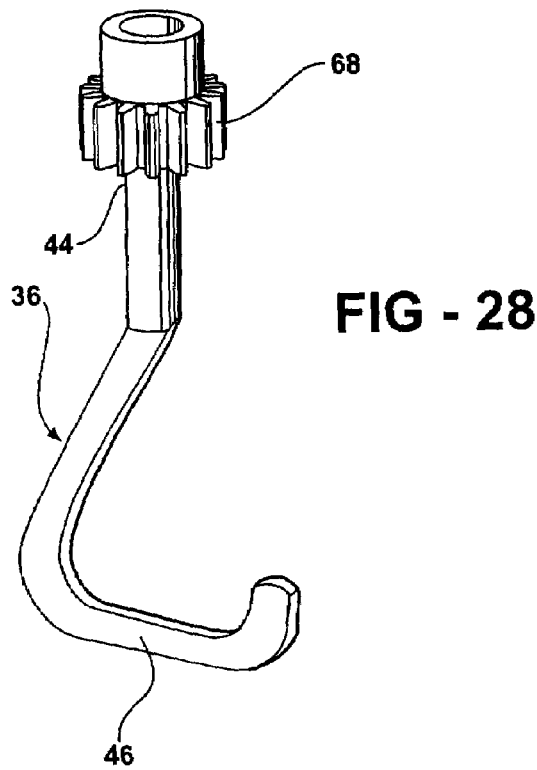
FIG. 28 is a perspective view of one embodiment of the second mixing paddle for use in the mixing assembly of the subject invention.
Figure 29:
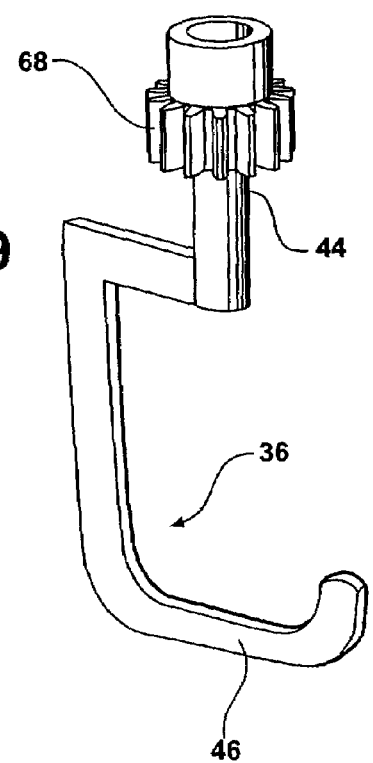
FIG. 29 is a perspective view of another embodiment of the second mixing paddle for use in the mixing assembly of the subject invention.
Figure 30:
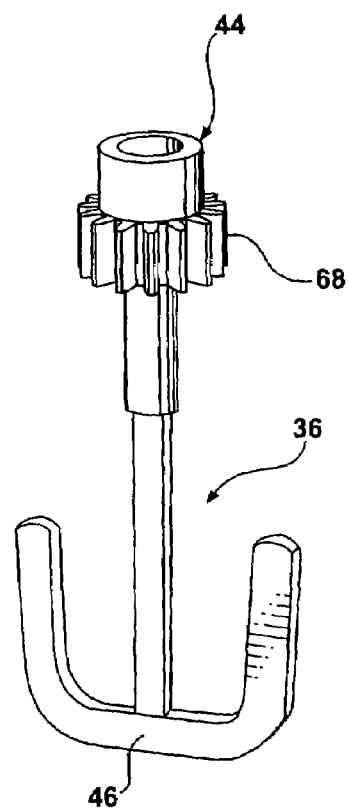
FIG. 30 is a perspective view of another embodiment of the second mixing paddle for use in the mixing assembly of the subject invention.
Figure 31:
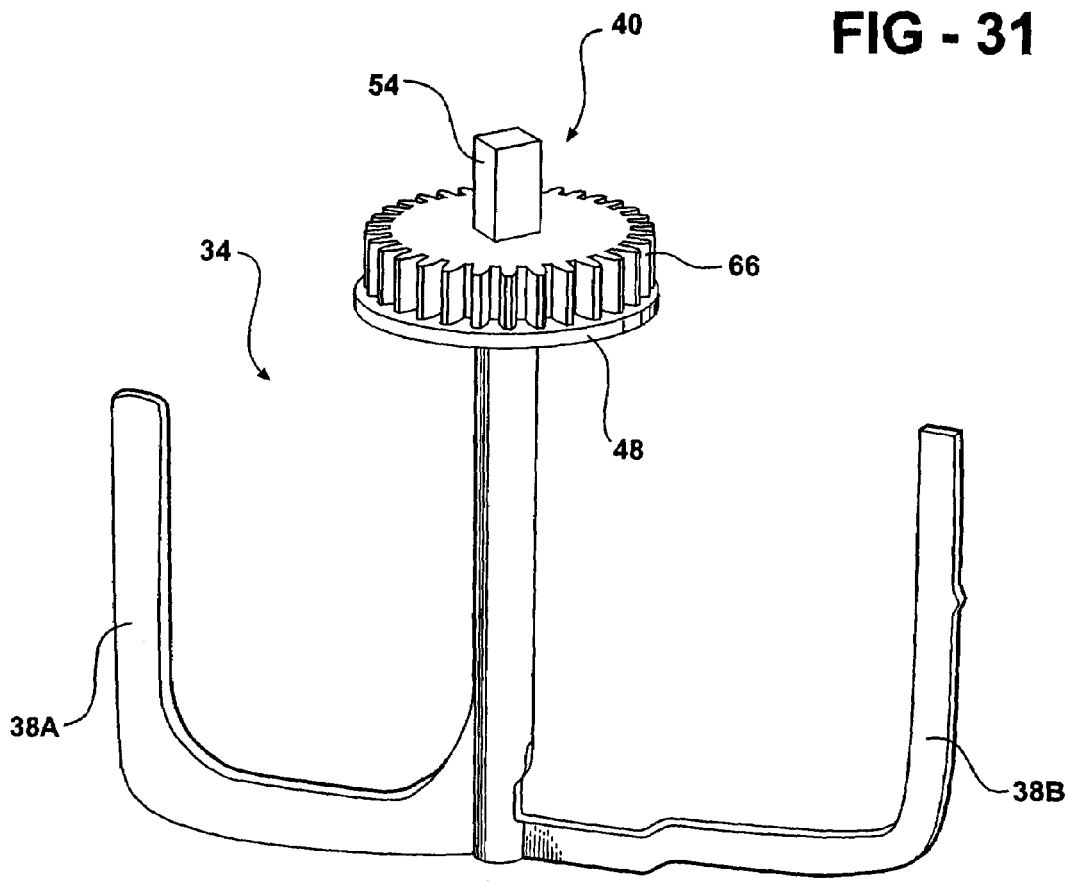
FIG. 31 is a perspective view of one embodiment of the first mixing paddle for use in the mixing assembly of the subject invention.
Figure 32:
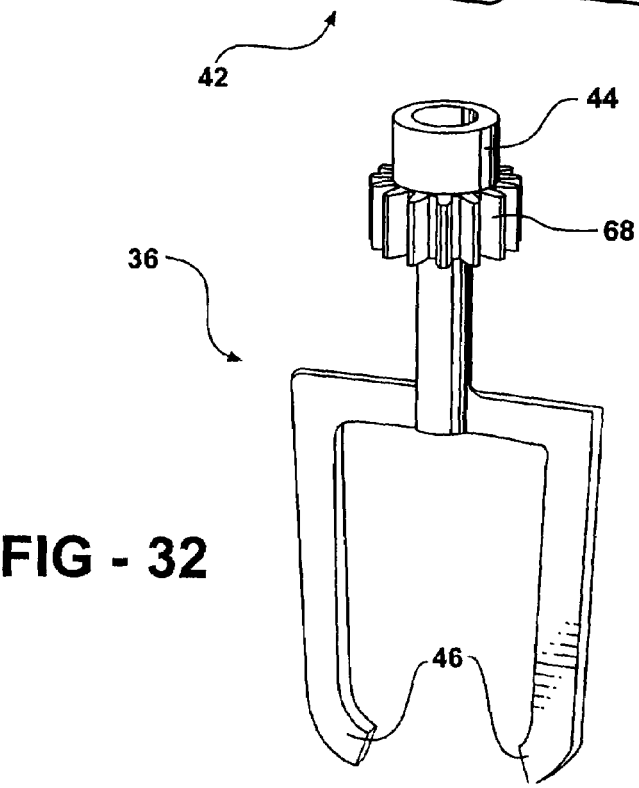
FIG. 32 is a perspective view of another embodiment of the second mixing paddle for use in the mixing assembly of the subject invention.
Figure 33:
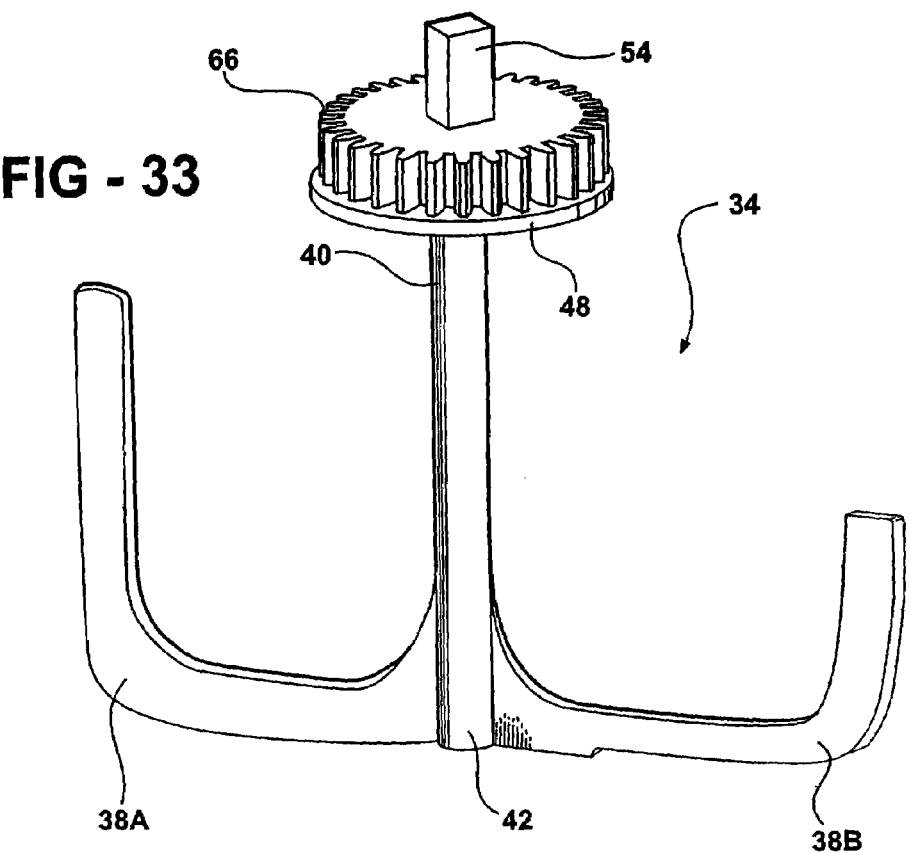
FIG. 33 is a perspective view of another embodiment of the first mixing paddle for use in the mixing assembly of the subject invention.
Figure 34:
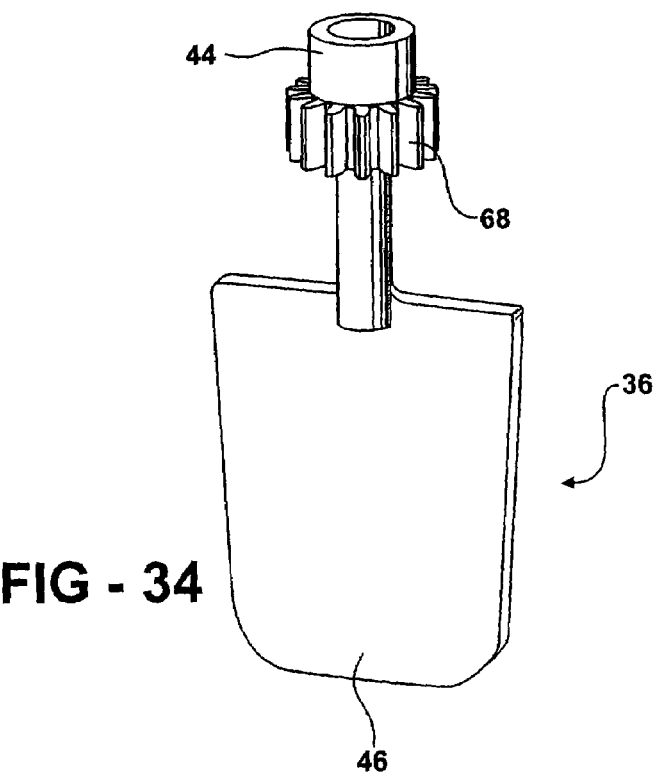
FIG. 34 is a perspective view of another embodiment of the second mixing paddle for use in the mixing assembly of the subject invention.
Figure 35:
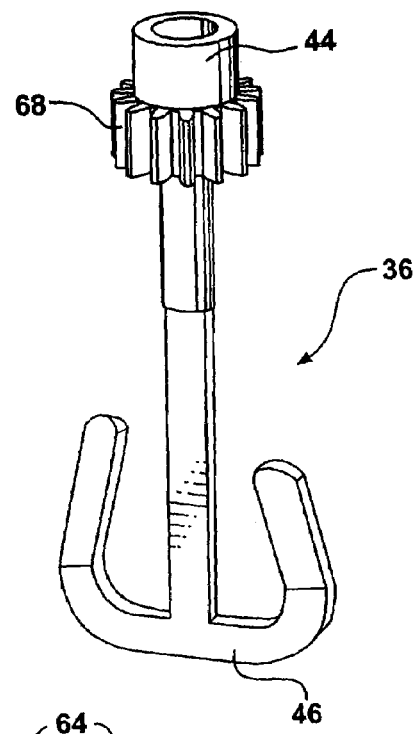
FIG. 35 is a perspective view of another embodiment of the second mixing paddle for use in the mixing assembly of the subject invention.
Figure 36:
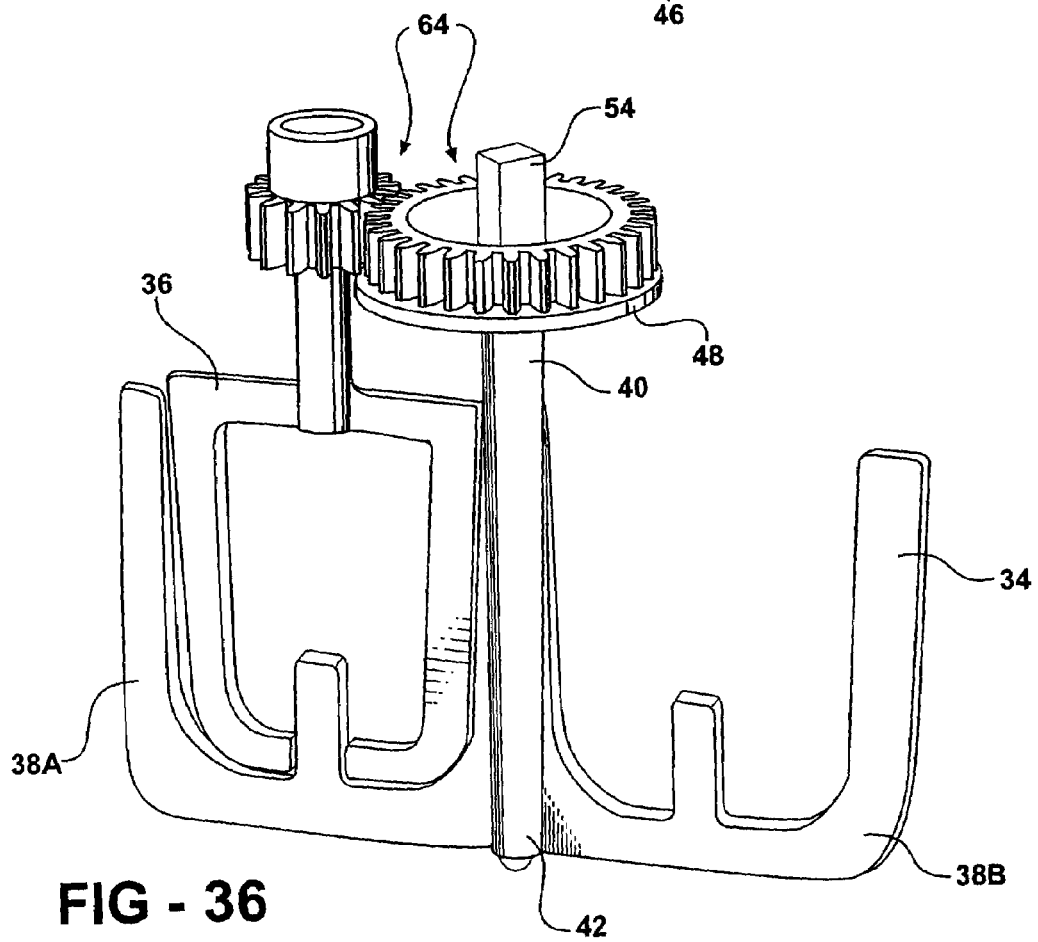
FIG. 36 is a perspective view of other embodiment of the first and second mixing paddles for use in the mixing assembly of the subject invention.

Referring primarily to FIGS. 22 through 43, wherein like numerals indicate like or corresponding parts throughout the several views, a mixing assembly for mixing bone cement is generally shown at 10. For ease of description, the mixing assembly 10 may also be referred to herein as a bone cement mixing bowl assembly. The mixing assembly 10 includes a housing 12 and a lid 14. The housing 12 is further defined as a bowl. Consequently, the housing 12 may be referred to herein as a bowl or a mixing bowl. The housing 12 includes at least one interior wall 16 and a base 18 for providing addition support and stability to the housing 12. As disclosed in FIGS. 23 and 24, the mixing assembly 10 also preferably includes a depression 20 that is defined within the housing 12. The significance of this depression 20 is described below.

The lid 14 is removably attached to the housing 12, and a sealed mixing chamber 22 is defined between the lid 14 and the interior wall 16 of the housing 12. Of course, this sealed mixing chamber 22 exists once the lid 14 is attached to the housing 12. The bone cement is mixed in the sealed mixing chamber 22. Preferably, a vacuum port 24 is defined within the lid 14. The vacuum port 24 is particularly adapted for attaching a source to create a vacuum within the mixing assembly 10, as desired. The vacuum removes fumes from the mixing assembly 10 and, more importantly, the vacuum pulls air/porosity out of the bone cement. Because the lid 14 is removably attachable to the housing 12, the lid 14 can be removed from the housing 12 to insert the bone cement and the lid 14 can be attached to the housing 12 as described additionally below.

The mixing assembly 10 also includes a handle 26. The handle 26 has a portion 28 that extends through the lid 14. The handle 26 is rotatable about the lid 14. More specifically, the handle 26 is rotatable in a first rotational direction. More specifically, a first sleeve 30 is defined within and extends entirely through the lid 14 for supporting the portion 28 of the handle 26. The portion 28 of the handle 26 extends through the first sleeve 30 to extend through the lid 14 and at least partially into the sealed mixing chamber 22. Furthermore, a second sleeve 32, that is at least partially spaced from the first sleeve 30, extends from the lid 14. The significance of this second sleeve 32 is described below.

The mixing assembly 10 of the subject invention also includes a first mixing paddle 34 and a second mixing paddle 36. These paddles 34, 36 are also referred to in the art as mixing blades. Preferably, the first mixing paddle 34 includes a plurality of vanes 38 for mixing the bone cement. It is most preferred that these vanes 38 are concave and that the plurality of vanes 38 includes a first vane 38A and a second vane 38B. This first vane 38A contacts the interior wall 16 for scraping the bone cement, and the second vane 38B is spaced from the interior wall 16 for spreading, i.e., smearing, the bone cement.

The scraping of the bone cement from the interior wall 16 of the housing 12 ensures that the bone cement is moved around within the sealed mixing chamber 22 such that sufficient mixing of the bone cement can occur, and the spreading of the bone cement by the second vane 38B breaks a top surface of the bone cement thereby releasing air and gas bubbles from the bone cement. In summary, the first vane 38A scrapes a consistent thickness of bone cement, and the second vane 38B smears this consistent thickness which ultimately results in more efficient removal of porosity from the bone cement. As disclosed in the Figures, the first mixing paddle 34 rotates beneath and around the second mixing paddle 36. More specifically, the vanes 38 of the first mixing paddle 34 rotate beneath and around the second mixing paddle 36. Various structures for both the first and second mixing paddles 34, 36 are disclosed in FIGS. 28-36. These various structures for the first and second mixing paddles 34, 36 are all significant because the first and second mixing paddles 34, 36 are interchangeable as desired.

Regardless of the particular structure for the first mixing paddle 34, the first mixing paddle 34 includes a first end 40 and a second end 42. The first end 40 of the first mixing paddle 34 is adjacent the lid 14 and is operatively coupled to the portion 28 of the handle 26. More specifically, the first end 40 of the first mixing paddle 34 is operatively coupled to the portion 28 of the handle 26 that extends through the first sleeve 30. As such, the first mixing paddle 34 rotates with rotation of the handle 26, preferably in a 1:1 ratio with the portion 28 of the handle 26. The second end 42 of the first mixing paddle 34, which is adjacent the housing 12 opposite the first end 40 of the first mixing paddle 34, is disposed in the depression 20.

Similarly, regardless of the particular structure for the second mixing paddle 36, the second mixing paddle 36 also includes a first end 44 and a second end 46. The first end 44 of the second mixing paddle 36 is adjacent the lid 14 and is disposed within the second sleeve 32. As such, the second sleeve 32 extends from the lid 14 for supporting the second mixing paddle 36, specifically the first end 44 of the second mixing paddle 36. The second end 46 of the second mixing paddle 36 is adjacent the housing 12 opposite the first end 44 of the second mixing paddle 36.

Preferably, an annular flange 48 is disposed about the first mixing paddle 34 at the first end 40, and at least one hole 50 is defined within the annular flange 48. The portion 28 of the handle 26 extends into the hole 50 to operatively couple the first mixing paddle 34 to the portion 28 of the handle 26. More specifically, as disclosed in FIG. 25, a first hole 50A and a second hole 50B are defined within the annular flange 48 of the first mixing paddle 34. The first hole 50A is defined 180° apart from the second hole 50B. In this embodiment, the portion 28 of the handle 26 includes a first set of tabs 52 (see FIG. 26) extending away from the handle 26. One of the tabs 52A extends into the first hole 50A to engage the annular flange 48 at the first hole 50A. The other of the tabs 52B extends into the second hole 50B to engage the annular flange 48 at the second hole 50B. The mechanical interaction between the first and second holes 50A, 50B and the tabs 52A, 52B operatively couples the first mixing paddle 34 to the portion 28 of the handle 26.

The first end 40 of the first mixing paddle 34 includes a post 54 that extends from the annular flange 48. The portion 28 of the handle 26 includes a socket 56. This socket 56 extends away from the handle 26 to receive the post 54 of the first mixing paddle 34. This mechanical interaction between the post 54 of the first mixing paddle 34 and the socket 56 of the handle 26 also operatively couples the first mixing paddle 34 to the portion 28 of the handle 26. Although not required, it is preferred that the post 54 and the socket 56 are rectangular.

The mixing assembly 10 also includes a centering post 58. This centering post 58 is disposed within the socket 56 of the portion 28 of the handle 26. A first resilient member 60 is disposed about the centering post 54, within the socket 56, and between the portion 28 of the handle 26 and the first end 40 of the first mixing paddle 34. The first resilient member 60 biases the first mixing paddle 34 which is described additionally below. Similarly, a second resilient member 62 is disposed within the second sleeve 32 between the lid 14 and the first end 44 of the second mixing paddle 36. The second resilient member 62 biases the second mixing paddle 36. As is understood by those skilled in the art, the first and second resilient members 60, 62 are also referred to in the art as biasing devices.

Figure 37:
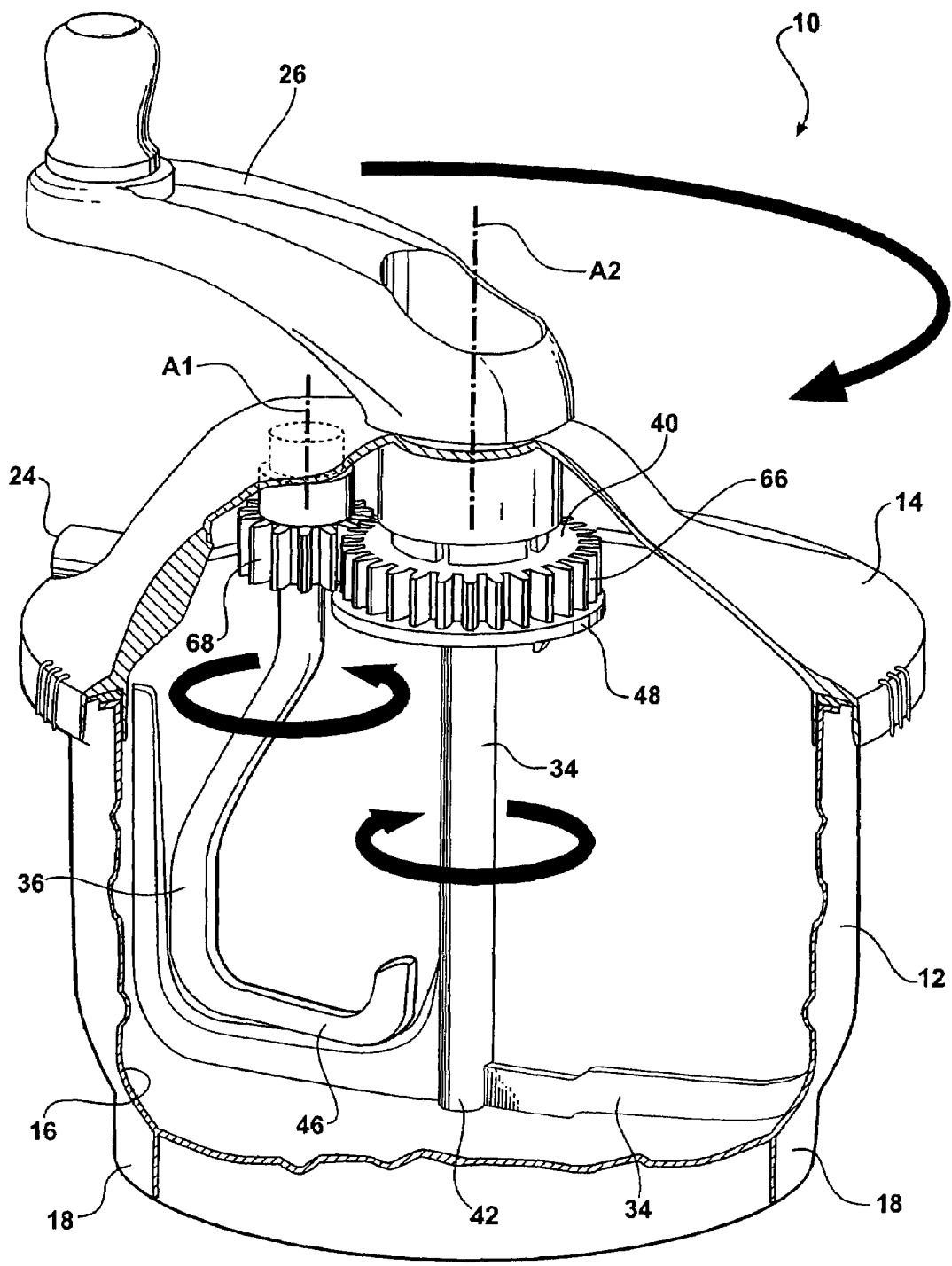
FIG. 37 is a partially cutaway perspective view of the mixing assembly according to another embodiment of the present invention that illustrates the portion of the handle and the first mixing paddle rotating in a first rotational direction and the second mixing paddle rotating in a second rotational direction.

The first mixing paddle 34 is operatively coupled to the portion 28 of the handle 26 for rotating with the portion 28 in the first rotational direction to mix the bone cement. The second mixing paddle 36 is operatively coupled to the first mixing paddle 34 for rotating opposite the portion 28 of the handle 26. As such, when the portion 28 and the first mixing paddle 34 rotate in the first rotational direction to mix the bone cement, the second mixing paddle 36 rotates in a second rotational direction that is opposite the first rotational direction also to mix the bone cement. As a result, it is only required that the handle 26 and its portion 28, and therefore the first mixing paddle 34, rotate in one rotational direction. This is represented in FIG. 37. Of course, if the handle 26, its portion 28, and the first mixing paddle 34 only rotate in one rotational direction, then a mechanical stop of some equivalent will be required to interact with, or otherwise engage, the handle 26, its portion 28, and/or the first mixing paddle 34. Such mechanical stops, which are known to those skilled in the art, would prevent rotation in a second rotational direction.

Figure 38:
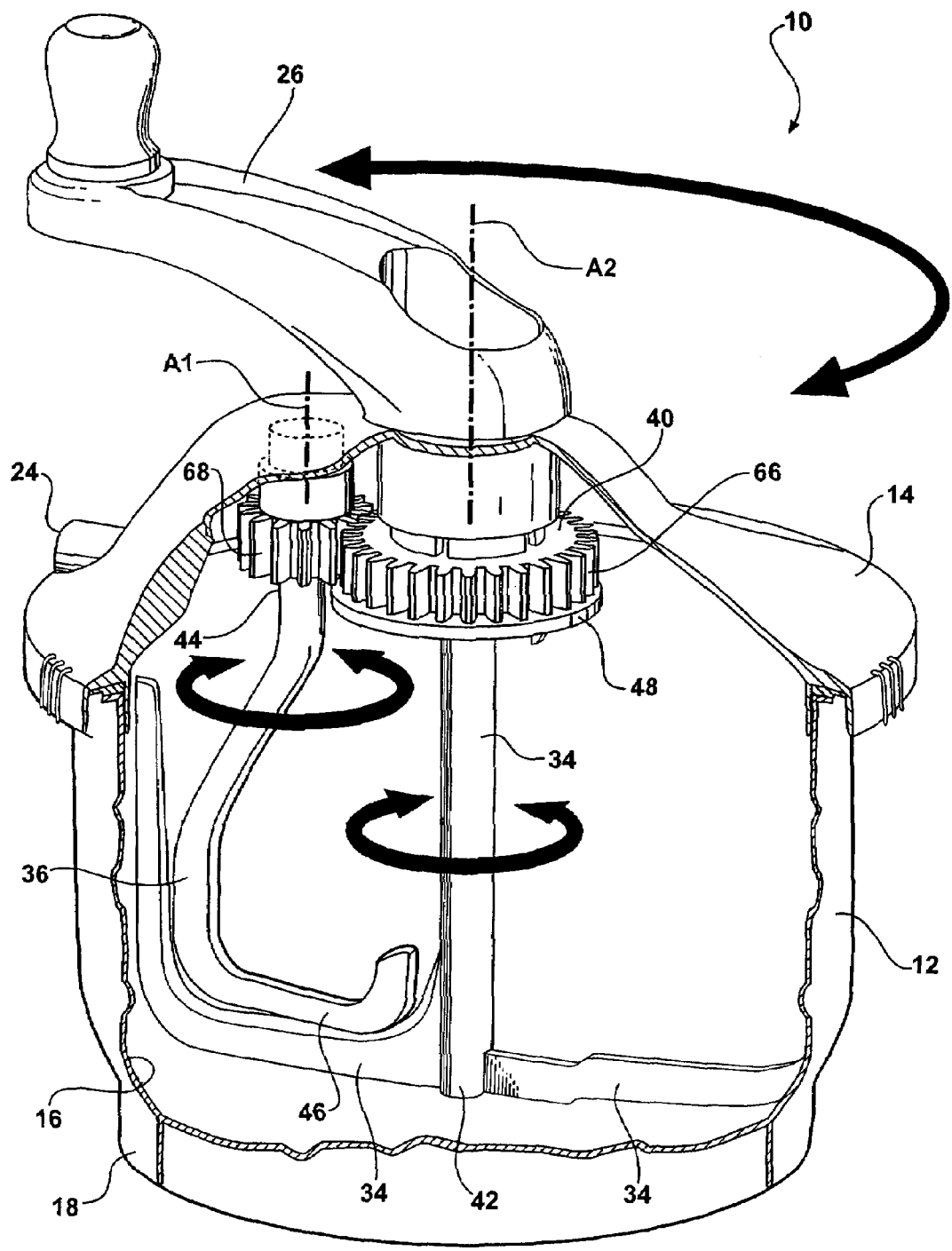
FIG. 38 is a partially cutaway perspective view of the mixing assembly according to another embodiment of the present invention that illustrates the portion of the handle and the first mixing paddle being rotatable is a first rotational direction and in a second rotational direction, and the second mixing paddle being rotatable in the first and second rotational direction so long as the second mixing paddle rotates opposite the portion and the first mixing paddle.

Although the portion 28 of the handle 26 and the first mixing paddle 34 need only be rotatable in one rotational direction, and the second mixing paddle 36 need only be rotatable in an opposite rotational direction, it is preferred that the portion 28 of the handle 26 and the first mixing paddle 34 are also rotatable in the second rotational direction that is opposite the first rotational direction. In this preferred embodiment, the second mixing paddle 36 is also operatively coupled to the first mixing paddle 34 such that the second mixing paddle 36 rotates in the first rotational direction when the portion 28 and the first mixing paddle 34 are rotating in the second rotational direction. This is represented in FIG. 38.

Furthermore, although not required, it is preferred that the first mixing paddle 34 is rotatable about a first fixed axis of rotation A1 and the second mixing paddle 36 is rotatable about a second fixed axis of rotation A2 that is different from the first fixed axis of rotation A1. In this preferred embodiment, the first and second fixed axes of rotation A1, A2 remain fixed throughout rotation of the first and second mixing paddles 34, 36. The depression 20 defined within the housing 12, which was originally described above, is aligned with the first fixed axis of rotation A1 to maintain the first fixed axis of rotation A1 and to stabilize the first mixing paddle 34 during rotation of the first mixing paddle 34.

A gear set 64 is disposed between the first mixing paddle 34 and the second mixing paddle 36. This gear set 64 operatively couples the second mixing paddle 36 to the first mixing paddle 34 such that the second mixing paddle 36 rotates opposite the portion 28 in the second rotational direction when the portion 28 and the first mixing paddle 34 rotate in the first rotational direction. Similarly, in the embodiment where the portion 28 and the first mixing paddle 34 are also rotatable in the second rotational direction, the gear set 64 operatively couples the second mixing paddle 36 to the first mixing paddle 34 such that the second mixing paddle 36 rotates opposite the portion 28 in the first rotational direction when the portion 28 and the first mixing paddle 34 rotate in the second rotational direction.

Preferably, the gear set 64 includes a first gear 66 associated with the first mixing paddle 34 and a second gear 68 associated with the second mixing paddle 36. More specifically, the first gear 66 is supported on the annular flange 48 of the first mixing paddle 34 and the second gear 68 is disposed at the first end 44 of the second mixing paddle 36. The second gear 68 is recessed into the second sleeve 32. Once the second mixing paddle 36 is assembled into the mixing assembly 10, and the second gear 68 is therefore recessed into the second sleeve 32, the first mixing paddle 34 is assembled into the mixing assembly 10 and the annular flange 48 of the first mixing paddle 34 at least partially overlaps the second gear 68 of the second mixing paddle 36. This overlay automatically retains the second mixing paddle 36 in the second sleeve 32. The first gear 66 mates with the second gear 68 to rotate the second mixing paddle 36 in the second rotational direction when the portion 28 and the first mixing paddle 34 rotate in the first rotational direction, and vice versa. It is to be understood that the gear set 64 may be alternatively designed such that the first and second gears 66, 68 are not required. As one non-limiting example, the gear set 64 could be a belt-drive system know to those skilled in the art.

Preferably, the mixing assembly 10 incorporates a gear ratio of the first gear 66 to the second gear 68 of 2:1. It is believed that this gear ratio provides optimum mixing of the bone cement by the first and second mixing paddles 34, 36. However, it is to be understood that other gear ratios can be incorporated into the mixing assembly 10 without varying the scope of the subject invention. It is also preferred that the first gear 66 and the second gear 68 are defined as spur gears. However, other gears known to those generally skilled in the mechanical arts may be utilized within the context of the subject invention.

Figure 39:
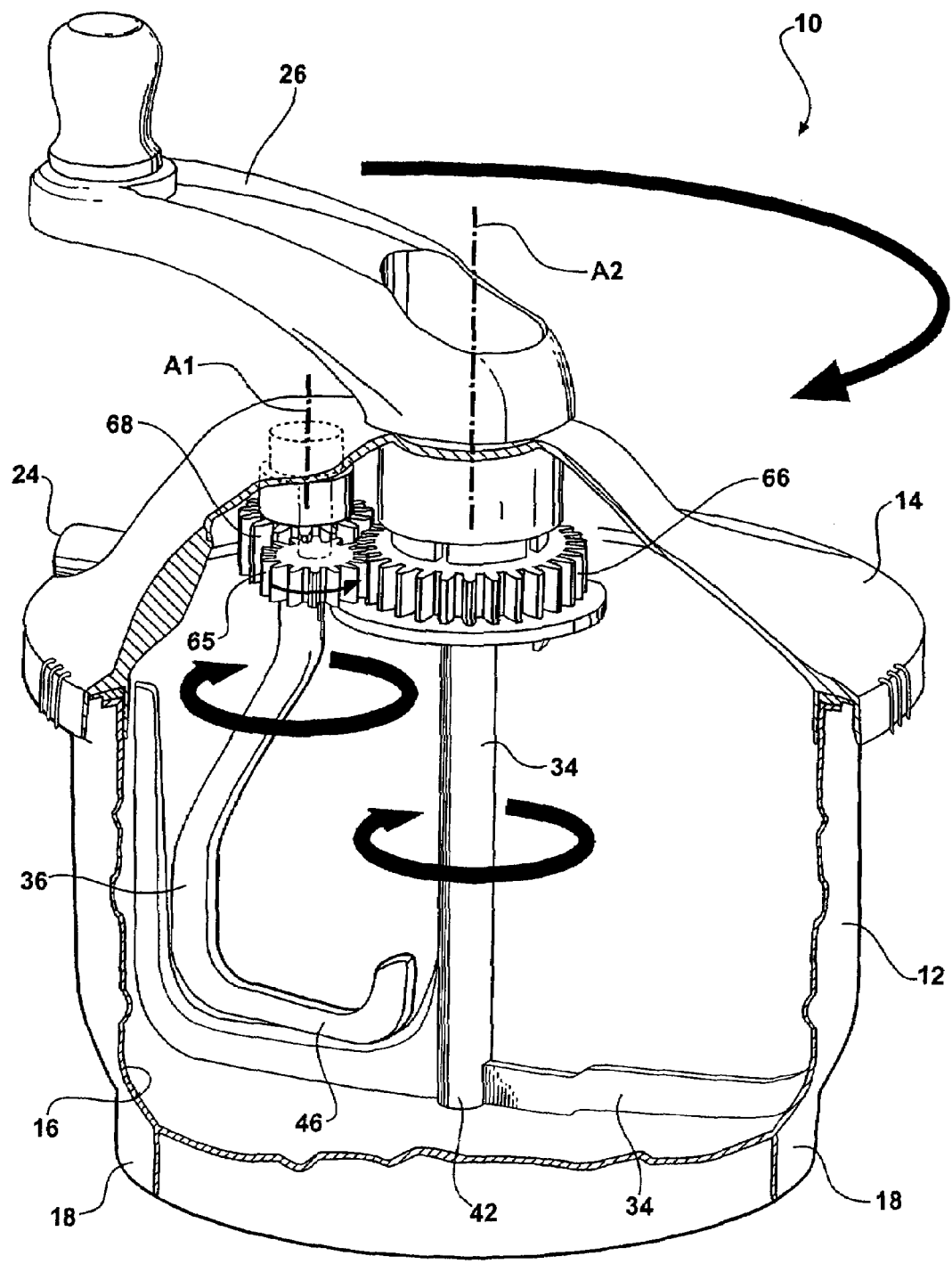
FIG. 39 is a partially cutaway perspective view of the mixing assembly according to another embodiment of the present invention that illustrates the portion of the handle, the first mixing paddle, and the second mixing paddle rotating in a first rotational direction.

It is to be understood by those skilled in the art that the gear set 64 may include additional gears beyond the first gear 66 and the second gear 68. For example, the gear set 64 may further include a third gear 65. If such an embodiment is desired, the first and second mixing paddles 34, 36 could rotate in the same rotational direction at the same time. Preferably then, the gear ratio would be established such that the first and second mixing paddles 34, 36 would rotate in the same rotational direction but about their respective fixed axes A1, A2 at different rotational speeds. The third gear 65 and the portion 28 of the handle 26 and the first and second mixing paddles 34, 36 all rotating in the same direction at the same time are represented in FIG. 39.

In preferred embodiments of the subject invention, the handle 26 is operatively coupled to the first mixing paddle 34 through the portion 28 of the handle 26 that extends into the mixing chamber 22. However, it is to be understood that, as particularly disclosed in FIGS. 13 and 14, the handle 26 can be operatively coupled to the second mixing paddle 36 instead of the first mixing paddle 34. In such an embodiment, it is apparent to those skilled in the art that the gear set 64 would require manipulation to accommodate the interaction between the handle 26 and the second mixing paddle 36.

In a further embodiment of the subject invention, the lid 14, which is removably attachable to the housing 12, is movable between an open position and a sealed position. The open position is particularly disclosed in FIG. 40, and the sealed position is particularly disclosed in FIG. 41. In the open position for the lid 14, the bone cement can be added to the housing 12. It is to be understood that the lid 14 can also be set on top of the housing 12, such that the bone cement cannot actually be added into the mixing chamber 22, yet the lid 14 is still in the open position. In other words, the lid 14 is not in the sealed position until the lid 14 is locked to the housing 12 as described additionally below. In the sealed position for the lid 14, the lid 14 is hermetically sealed to the housing 12 to define the sealed mixing chamber 22 between the lid 14 and the interior wall 16 of the housing 12. The terminology "hermetically" is merely intended to indicate that the sealed mixing chamber 22 is impervious to external influences, of course with the exception of the vacuum. As described above, the bone cement is mixed in the sealed mixing chamber 22.

This particular embodiment of the subject invention only requires one mixing paddle 34. For descriptive purposes, the one mixing paddle 34 will be referred to as the first mixing paddle 34. As in the embodiment described above, the first mixing paddle 34 is operatively coupled to the portion 28 of the handle 26 for rotating with the portion 28. The first mixing paddle 34 is movable between an extended position when the lid 14 is in the open position and a retracted position where the mixing paddle is adapted to scrape the bone cement from the interior wall 16 when the lid 14 is in the sealed position.

The first resilient member 60 is disposed between the portion 28 of the handle 26 and the first mixing paddle 34. Preferably, the first resilient member 60 is a compression spring. However, it is to be understood that the first resilient member 60 may be other types of biasing devices including, but not limited to, torsion springs and leaf springs. Of course, if alternative first resilient members 60 are utilized, then persons skilled in the art understand that certain modifications structural modifications between the portion 28 of the handle 26 and the first mixing paddle 34 may be required.

As described above, the first resilient member 60 is disposed about the centering post 54 and within the socket 56. The first resilient member 60 normally-biases the first mixing paddle 34 into the extended position. Importantly, the first resilient member 60 biases the first and second mixing paddles 34, 36 downward into the housing 12 whether the mixing assembly 10 is being utilized with, or without vacuum.

The first resilient member 60 also compresses to permit the first mixing paddle 34 to retract into the retracted position. The first resilient member 60 compresses in response to contact between the first mixing paddle 34 and the interior wall 16 of the housing 12 as the lid 14 is moved from the open position to the sealed position, i.e., as the lid 14 is put on the housing 12. As such, the lid 14 can be hermetically sealed to the housing 12 in the sealed position, yet the first mixing paddle 34 can still scrape the bone cement from the interior wall 16, specifically from a bottom 70 of the housing 12, due to the normal biasing of the first resilient member 60.

Figure 40:
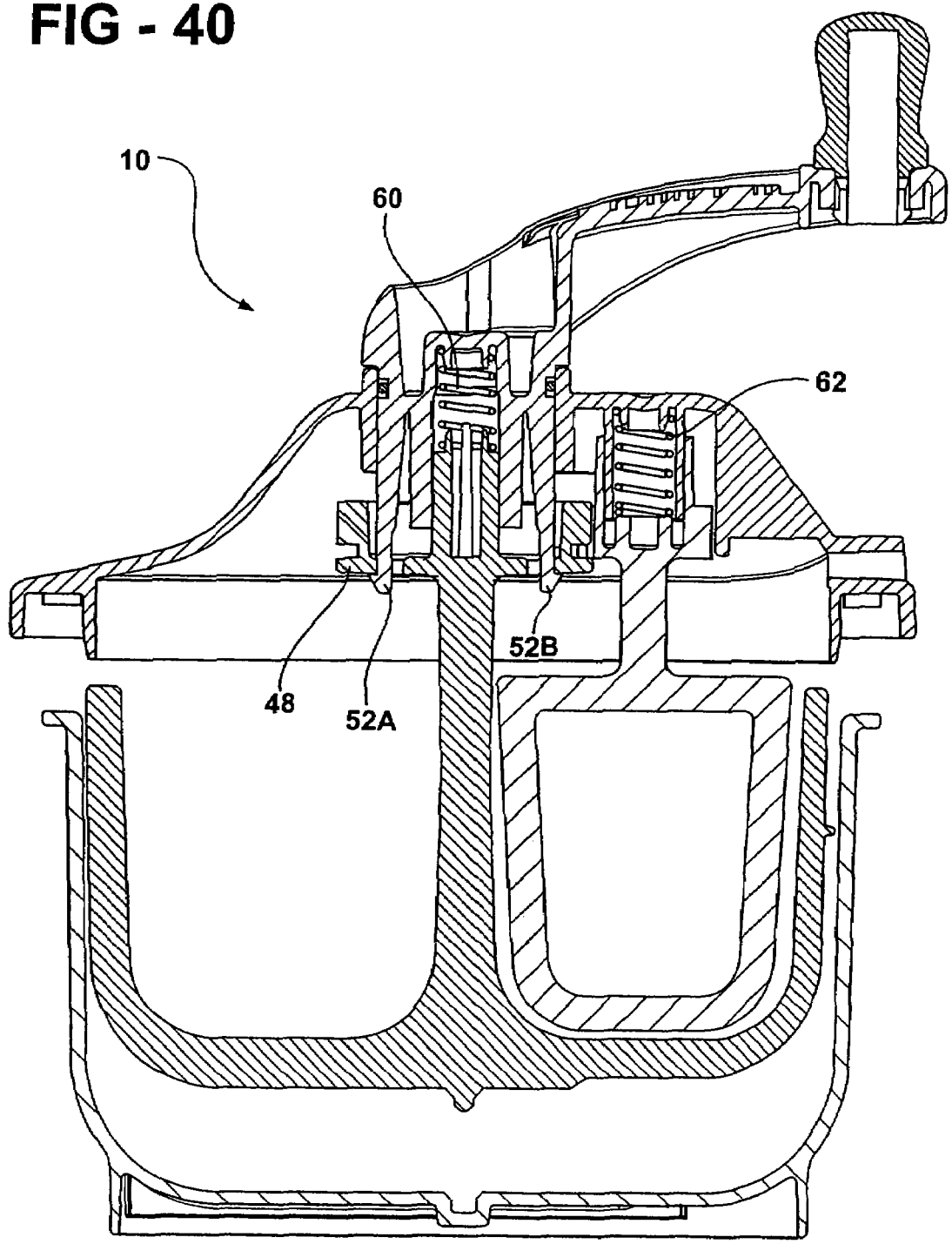
FIG. 40 is a cross-sectional view of the mixing assembly illustrating the lid in an open position with no gap between a first set of tabs and an annular flange of the first mixing paddle.
Figure 41:
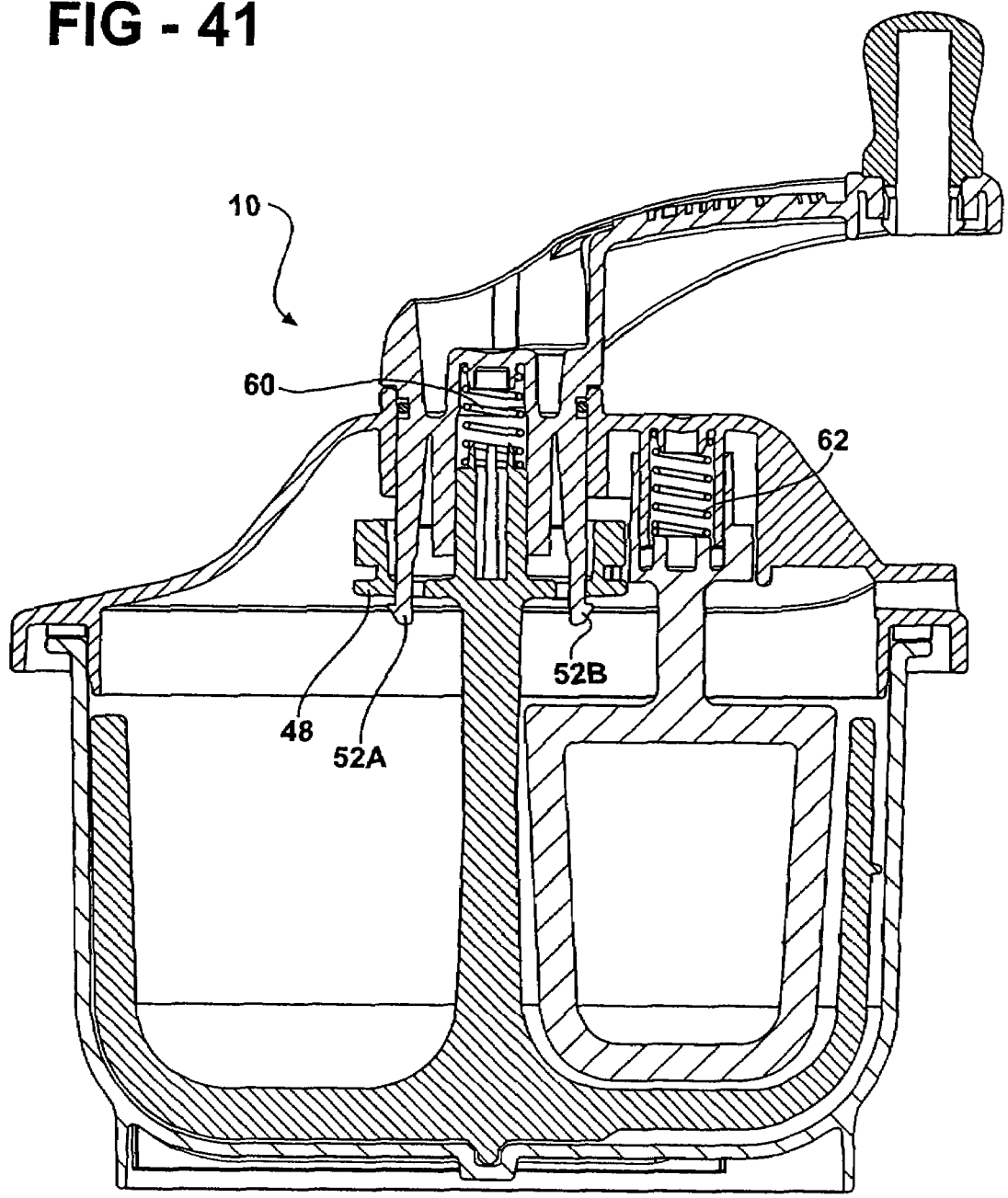
FIG. 41 is a cross-sectional view of the mixing assembly disclosed in FIG. 40 illustrating the lid in a sealed position with a gap between the first set of tabs and the annular flange of the first mixing paddle.
Figure 42:
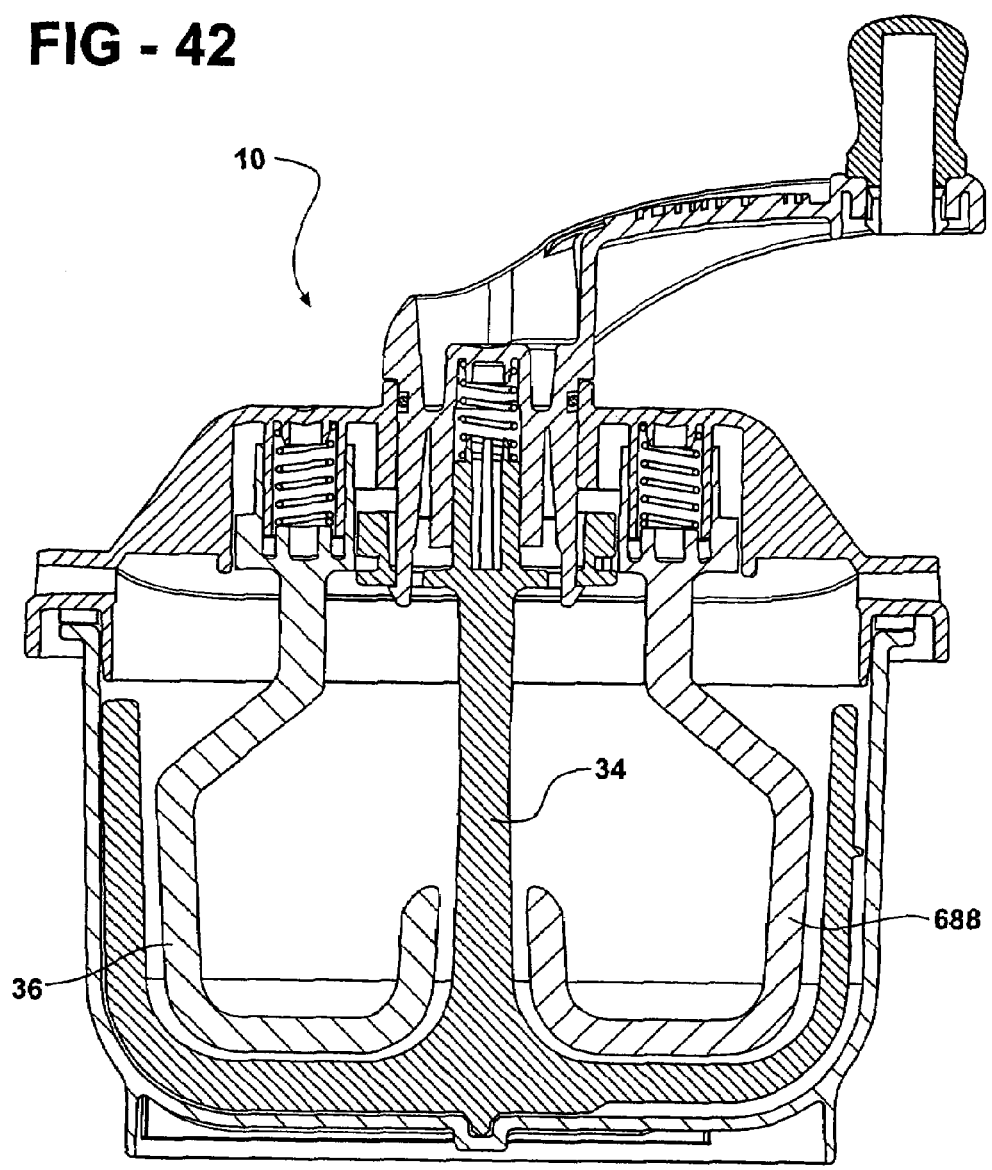
FIG. 42 is a cross-sectional view of the mixing assembly according to another embodiment of the present invention illustrating a third mixing paddle.
Figure 43:
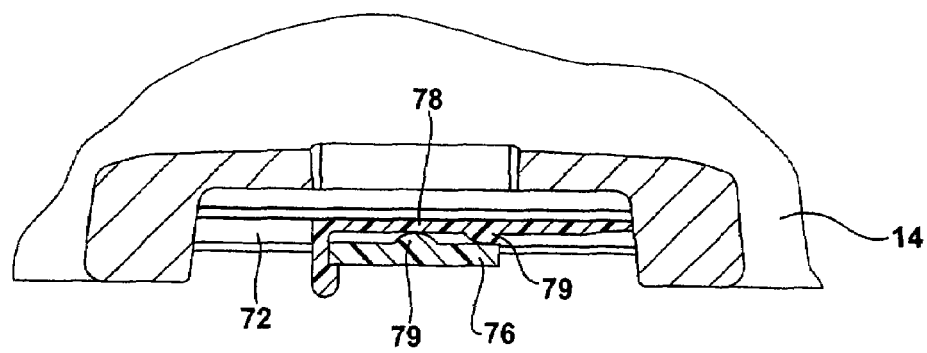
FIG. 43 is a partially cross-sectional side view of the mixing assembly illustrating tabs on the lid and ramps on a rim of the housing for locking the lid to the housing in the sealed position.

Due to the first resilient member 60, there is no space or gap between the first set of tabs 52 extending from the portion 28 of the handle 26 and the annular flange 48 of the first mixing paddle 34 when the lid 14 is in open position (refer to the relationship between the first set of tabs 52 and the annular flange 48 in FIG. 40). However, as the lid 14 is being moved, i.e., rotated, about the housing 12 from the open position into the sealed position, the first mixing paddle 34 contacts the bottom 70 of the housing 12 thereby forcing the first mixing paddle 34 upward against the normal bias of the first resilient member 60 causing the first resilient member 60 to compress. As a result, there is a minor space or gap established between the first set of tabs 52 and the annular flange 48 (refer to the relationship between the first set of tabs 52 and the annular flange 48 in FIG. 41). The significance of this biasing and compression of the first resilient member 60 relative to the first mixing paddle 34 is that a complete hermetic seal can be established while the first mixing paddle 34 is still biased to contact the bottom 70 of the housing 12 such that the first mixing paddle 34 can still effectively scrape the bone cement.

More specifically, it is the second end 42 of the first mixing paddle 34 that actually contacts the bottom 70 of the housing 12 as the lid 14 is put on the housing 12. This second end 42 also contacts the depression 20 defined within the housing 12.

The housing 12 further includes a rim 72. The lid 14 mates with the rim 72 upon moving from the open, i.e., unlocked, position to the sealed, i.e., locked, position. The mating of the lid 14 and the rim 72 hermetically seals the lid 14 to the housing 12. Preferably, a compression sealing member 74 is disposed between the lid 14 and the rim 72. Furthermore, to adequately retain the lid 14 attached to or on the housing 12, a plurality of tabs 76, referred to as a second set of tabs 76, are disposed about the lid 14 and a plurality of locking ramps 78 are disposed about the rim 72 of the housing 12. Upon movement of the lid 14 from the open position to the sealed position, the tabs 76 of the lid 14 engage the ramps 78 of the housing 12 to lock the lid 14 to the housing 12. As disclosed in FIG. 43, the tabs 76 and the ramps 78 include mating nubs 79 to enhance locking.

Figure 1:
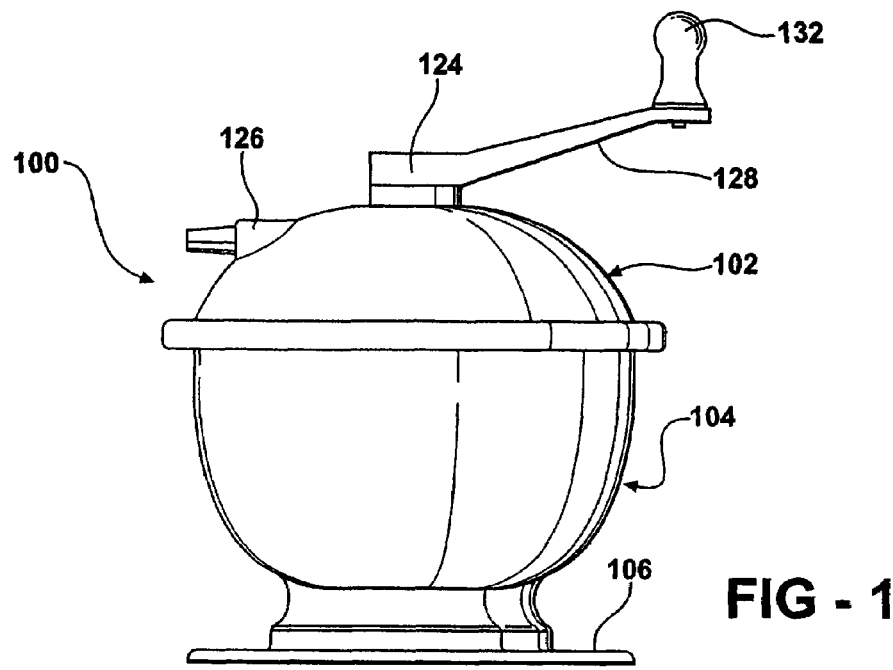
FIG. 1 is a view of a mixing assembly according to one embodiment of the present invention.
Figure 2:
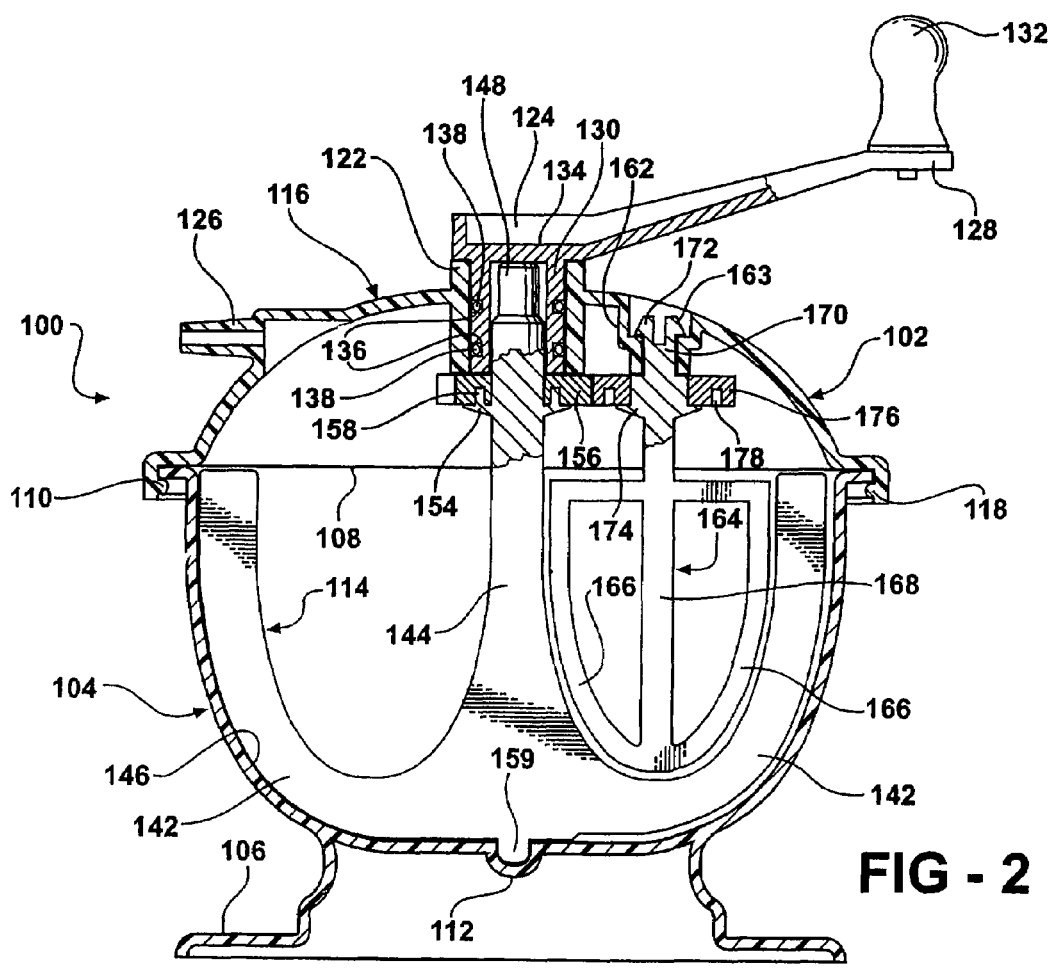
FIG. 2 is a partially cross-sectional view of the mixing assembly of FIG. 1.
Figure 3:
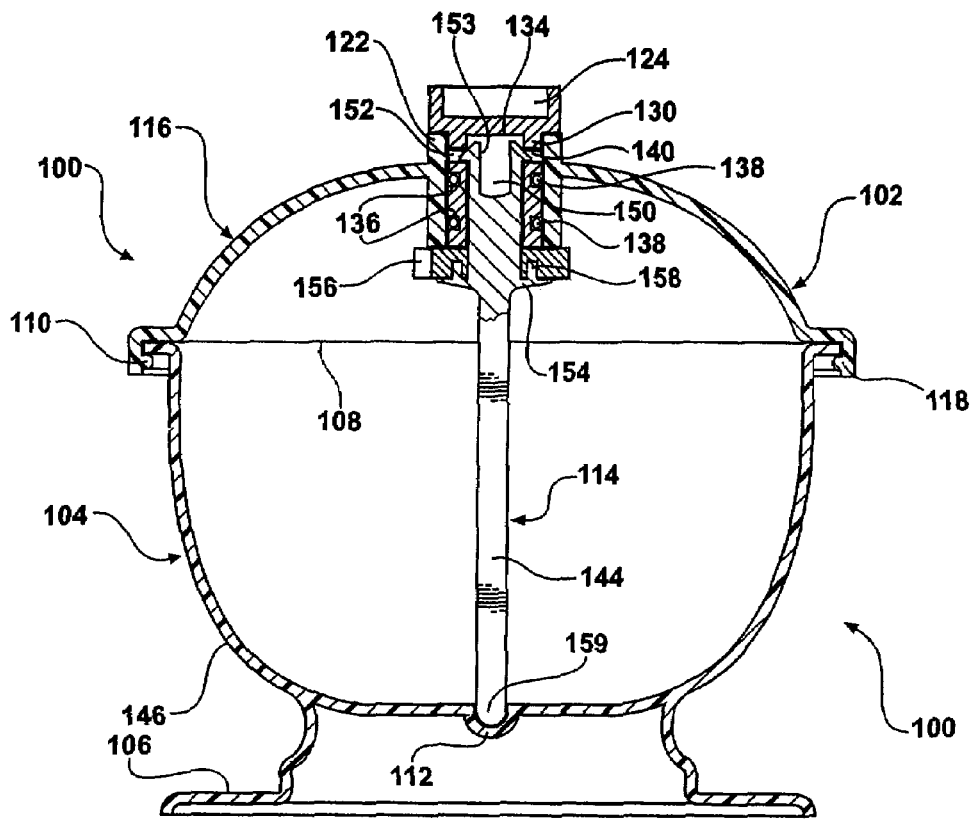
FIG. 3 is another partially cross-sectional view of the mixing assembly of FIG. 1.

Referring now to FIGS. 1 through 3, in a further embodiment of the mixing bowl assembly 100, the lid 116 includes a seal 118 for creating a seal between the lid 116 and the annular flange lip 110 of the housing 104 and further includes a connection for securing the lid 116 to the housing 104. In one embodiment, the connection comprises a plurality of projections 111 extending from the housing 104 that engage a plurality of locking ramps 113 in the lid assembly 102, thereby securing the lid assembly 102 to the housing 104. The lid assembly 102 may be mated to the housing 104 by any other suitable connection such as threads or snap fittings. The lid 116, which is a component of the lid assembly 102, further includes a first cylindrical sleeve 122 for mounting a rotatable handle assembly 124 thereon. The first cylindrical sleeve 122 receives the rotatable handle assembly 124, to be described below. The lid assembly 102 further includes a vacuum port 126 for attaching a vacuum source and creating a vacuum within the mixing bowl assembly 100.

As shown in FIGS. 1 through 6, the rotatable handle assembly 124 includes a grasping end 128 and a locking end 130 and extends outwardly from the lid 116. The grasping end 128 includes a knob 132 disposed thereon allowing a user to grasp the rotatable handle assembly 124 and rotate the handle assembly 124 in either a clockwise rotational direction, a counterclockwise rotational direction, or both. The knob 132 may have a tab connector or any other suitable mating connector, wherein the handle assembly 124 is adapted for receiving the knob 132. The locking end 130 includes a socket 134 adapted for receiving a first end 148 of the first mixing paddle 114. The socket 134 includes a plurality of external grooves 136, each of which includes a gasket 138 disposed therein for providing a seal between the locking end 130 of the rotatable handle assembly 124 and the first cylindrical sleeve 122. Preferably the gaskets 138 are O-rings. The socket 134 further includes at least one recess 140 adapted to retain the first mixing paddle 114, described below, such that one full rotation of the handle assembly 124 causes the first mixing paddle 114 to complete one full rotation.

Figure 4:
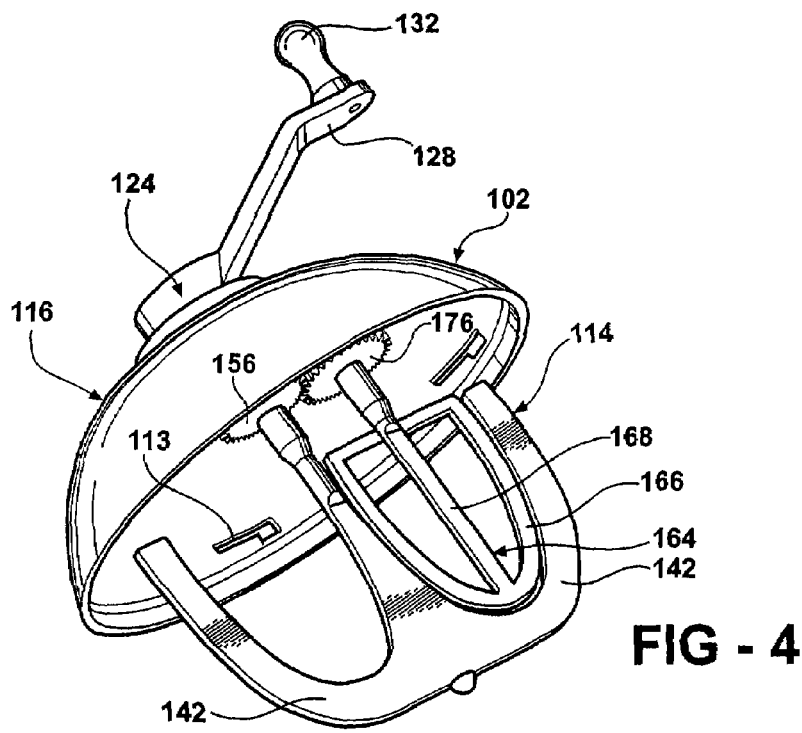
FIG. 4 is a perspective view illustrating, in particular, a lid, a handle, first and second mixing paddles, and a gear set according to the mixing assembly of FIG. 1.
Figure 5:
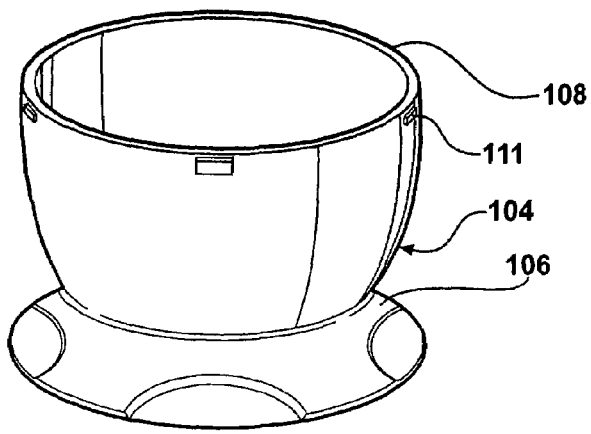
FIG. 5 is a perspective of view of a housing of the mixing assembly of the present invention.
Figure 6:
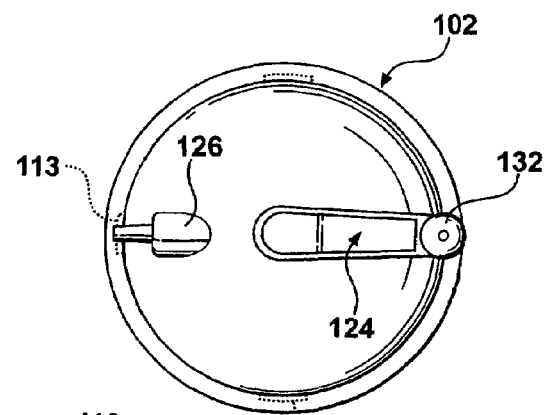
FIG. 6 is a top view of the lid illustrating the handle and a vacuum port defined within the lid.

Referring to FIGS. 2 through 4, the first mixing paddle 114 includes a plurality of concave vanes 142 disposed about a central rotating shaft 144 defining a central rotational axis wherein the plurality of concave vanes 142 extend from the central rotating shaft 144 and one contacts a wall 146 of the housing 104 while the other is spaced from the wall 146. This permits the vanes 142 to both scrape the cement from the wall 146 and to spread the cement. The central rotating shaft 144 includes the first end 148, which includes a slot 150 and at least one beveled tab 152 disposed thereon. The beveled tab 152 is located on a flexible arm 153 and adapted for mating with the at least one recess 140 in the socket 134 of the rotatable handle assembly 124 such that when the first end 148 of the central rotating shaft 144 is inserted into the socket 134 of the handle assembly 124, the tab 152 snaps into the recess 140 thereby securing the first mixing paddle 114 to the handle assembly 124. This allows the first mixing paddle 114 to rotate in accordance with the rotation of the handle assembly 124 while the central rotational axis remains in a fixed position relative to the handle assembly 124. Preferably, the socket 134 includes at least two recesses 140 and the first end 148 includes two beveled tabs 152. In this embodiment and all embodiments described below the first mixing paddle 114 is releasably secured to the handle assembly 124 or lid assembly 102, as described below. This permits a user to remove and replace the first mixing paddle 114 with another first mixing paddle having a different paddle design or other shape change that may be required by the particular cement being mixed.

As shown in FIGS. 2 and 3, the central rotating shaft 144 further includes a first annular flange 154 disposed thereon for supporting a first gear 156. The first annular flange 154 includes a plurality of tabs 158 disposed thereon for securing the first gear 156 to the first annular flange 154 such that the first gear 156 rotates in accordance with the handle assembly 124. The central rotating shaft 144 further includes a second end 159 juxtaposed between the plurality of concave vanes 142 and received into the depression 112 in the housing 104 for maintaining the axis of rotation of the first mixing paddle 114 in the fixed position and for stabilizing the paddle 114 during rotation.

Referring back to FIG. 2, the lid assembly 102 further includes a second cylindrical sleeve 162 disposed therein, with the sleeve 162 adapted to mount a second mixing paddle 164 having a plurality of vanes 166 extending radially from a second rotating shaft 168 defining a second rotational axis. The second rotating shaft 168 is spaced from the central rotating shaft 144 of the first mixing paddle 114 such that the plurality of concave vanes 142 of the first mixing paddle 114 rotate beneath and around the second mixing paddle 164. The second mixing paddle 164 includes a first end 170 having a plurality of tabs 172 thereon. The sleeve 162 includes a widened area 163 for receiving and securing the rotating tabs 172, thereby securing the second mixing paddle 164. As described above for the first mixing paddle 114 in this and all other embodiments this is a releasable connection so a user can remove and replace the mixing paddle as required. The second rotating shaft 168 includes a second annular flange 174 disposed thereon for supporting a second gear 176. The second annular flange 174 includes a plurality of tabs 178 disposed thereon for securing the second gear 176 to the second mixing paddle 164. Moreover, the second gear 176 is coupled with the first gear 156 such that when the handle assembly 124 is rotated in a first direction, thereby causing the first mixing paddle 114 to rotate in the first direction, the second mixing paddle 164 rotates in a second direction opposite of the first direction and the second rotational axis remains in its fixed position.

Figure 7:
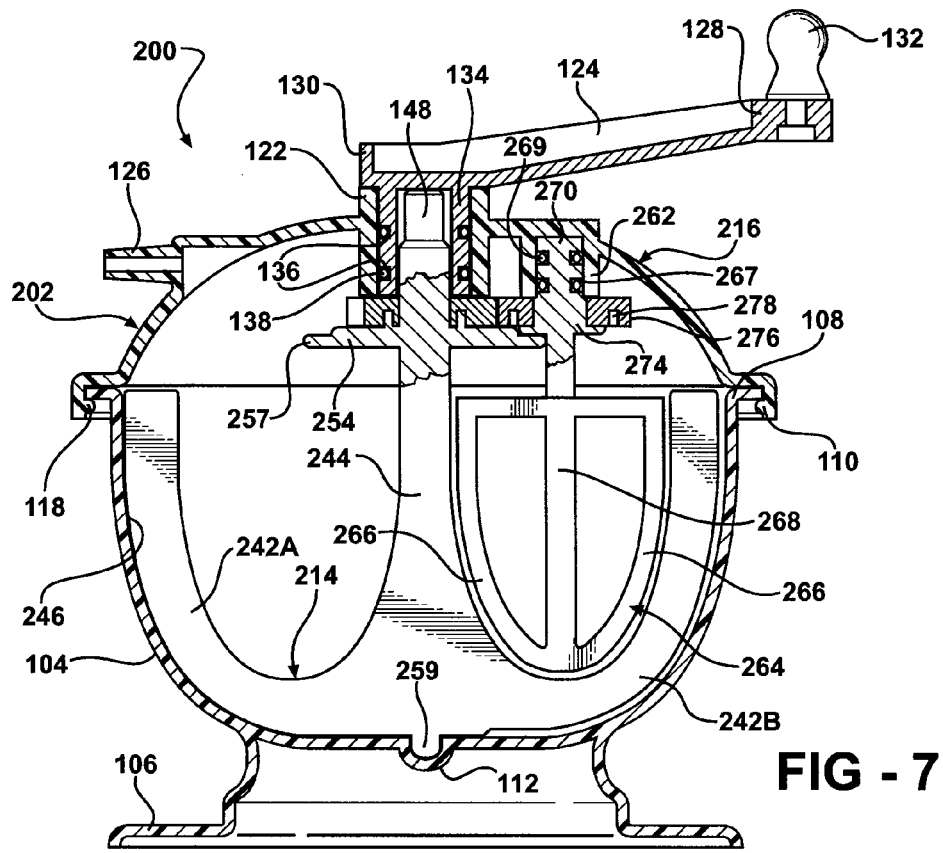
FIG. 7 is a partially cross-sectional view of the mixing assembly according another embodiment of the present invention.
Figure 8:
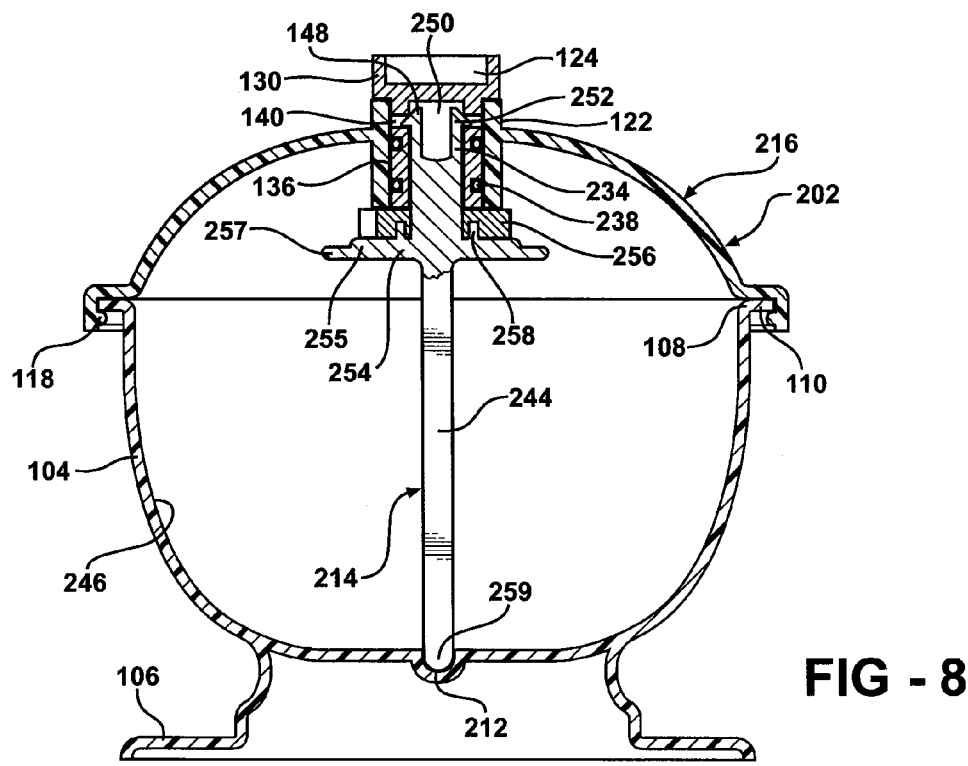
FIG. 8 is another partially cross-sectional view of the mixing assembly of FIG. 7.

Referring to FIGS. 7 and 8, another embodiment of the bone cement mixing bowl assembly of the present invention is generally shown at 200. Similar to the embodiment discussed above, the mixing bowl assembly 200 includes a housing 104 as described above and a lid assembly 202.

The lid assembly 202 includes a lid 216 as described above with regard to covering and sealing the housing 104 and as shown in FIG. 4, a rotatable handle assembly 124 as described above and shown in FIGS. 1 through 4. The lid assembly 202 includes a first mixing paddle 214 having a plurality of concave vanes including a first vane 242A and a second vane 242B that extend radially outwardly from a central rotating shaft 244 defining a central rotational axis. The first vane 242A is dimensioned to closely approach an interior wall 246 of the housing 204 so as to, like vane 38A, scrape cement off the interior wall 246. It is further clear from FIG. 7 that, in this process, the first vane 242A scrapes cement off the base of the interior wall 246, the section of the wall that defines a bottom of an interior space of the housing 104. The second vane 242B, like vane 38B, is shaped so its outer edge is spaced further from the interior wall 246. Consequently, when the first mixing paddle 214 is rotated, the second vane 242B, in a manner similar to vane 38B, smears the cement around the interior wall 246. Both the first 242A and second 242B vanes have inner edges located inwardly of their outer edges that are spaced outwardly from the central rotating shaft 244. Thus, within the housing interior space there is a space between the central rotating shaft 244 and the inner edges of the vanes 242A and 242B. The central rotating shaft 244 includes a first end 148 which includes a slot 250 and at least one beveled tab 252 disposed thereon. The beveled tab 252 is located on a flexible arm 253 and is adapted for mating with the recess 140 in the socket 134 of the rotatable handle assembly 124 such that when the first end 148 of the central rotating shaft 244 is inserted into the socket 134 of the handle assembly 124, the tab 252 snaps into the recess 140 thereby securing the first mixing paddle 214 to the handle assembly 124. This allows the first mixing paddle 214 to rotate in accordance with rotation of the handle assembly 124 while the central rotational axis remains in a fixed position relative to the handle assembly 124. Preferably, the socket 134 includes at least two recesses 140 and first end 148 includes two beveled tabs 252.

Referring to FIG. 8, the central rotating shaft 244 further includes a beveled annular flange 254 having first 255 and second 257 layers disposed thereon for supporting a first gear 256. The first layer 255 of the beveled annular flange 254 includes a plurality of tabs 258 disposed thereon for securing the first gear 256 to the beveled annular flange 254 such that the first gear 256 rotates in accordance with the handle assembly 124. The central rotating shaft 244 further includes a second end 259 juxtaposed between the first 242A and second 242B vanes and extending therefrom into a depression 212 in the housing 204 for maintaining the axis of rotation of the first mixing paddle 214 and for stabilizing the first mixing paddle 214 during rotation.

As shown in FIGS. 7 and 8, the lid assembly 202 further includes a closed-end sleeve 262 disposed therein, with the sleeve 262 adapted to mount a second mixing paddle 264 having a plurality of vanes 266 that extend radially from a second rotating shaft 268 defining a second rotational axis. The second rotating shaft 268 is spaced from the central rotating shaft 244. The second rotating shaft 268 includes a plurality of annular grooves 267, each of which has a gasket 269 to provide a seal between the second rotating shaft 268 and the sleeve 262. Collectively, the mixing paddles 214 and 264 are shaped so that, as the second mixing paddle 264 is rotated, each vane 266 of the second mixing paddle 264 rotates towards and then away from the central rotating shaft 244 and also towards and away from the inner edge of each vane 242A, 242B of the first mixing paddle 214. Preferably, the gaskets 269 are O-rings. The second rotating shaft 268 is spaced from the central rotating shaft 244 of the first mixing paddle 214 such that the vanes 242A, 242B of the first mixing paddle 214 rotate around and beneath the second mixing paddle 264. A first end 270 of the second rotating shaft 268 is adapted to be received into the sleeve 262 such that when the first end 270 of the second rotating shaft 268 is inserted into the sleeve 262 the second mixing paddle 264 rotates in a fixed position. The second rotating shaft 268 includes a second annular flange 274 disposed thereon for supporting a second gear 276. The second annular flange 274 includes a plurality of tabs 278 disposed thereon for securing the second gear 276 to the second mixing paddle 264. Further, the second annular flange 274 is aligned with the first layer 255 of the beveled annular flange 254 and rests on the second layer 257 such that the second layer 257 rotates beneath the second annular flange 274 and provides increased support and stability to the second mixing paddle 264, which is important when the cement gets thick and rotation becomes more difficult. Moreover, the second gear 276 engages with the first gear 256 such that when the handle assembly 224 is rotated in a first direction, thereby causing the first mixing paddle 214 to rotate in the first direction, the second mixing paddle 264 rotates in a second opposite direction while the second rotational axis remains in its fixed position. Owing to the above described relationship of the mixing paddles 214, 264, as a consequence of the rotation of each vane 266 of the second mixing paddle 264 towards the central rotating shaft 244, each vane 266 of the second mixing paddle 264 pushes bone cement-forming components towards and away from the central rotating shaft 244 to foster mixing of the cement. The rotation of the vanes 266 of the second mixing paddle 264 towards and away from the inner edges of the vanes 242A, 242B of the first mixing paddle 214 likewise pushes bone cement-forming components around the vanes 242A, 242B to further foster mixing of the cement. Also in this process, the vanes 266 of the second mixing paddle 264 push the bone cement-forming components off the sections of the vanes 242A, 242B above the bottom of the housing interior space away from the vanes 242A, 242B. As is further apparent from FIGS. 7 and 8, the mixing paddles 214, 264 are further arranged so that, during the simultaneous rotation of the mixing paddles 214, 264, there is at least one instance when the mixing paddles 214, 264 are aligned such that the vanes 242A, 242B of the first mixing paddle 214 and the vanes 266 of the second mixing paddle 264 are coplanar.

Referring to FIG. 9, a bone cement mixing bowl assembly according to another embodiment of the present invention is generally shown at 300. The mixing bowl assembly 300 includes a lid assembly 302 along with the housing 104, the rotatable handle assembly 124 and the first mixing paddle 114 shown in the embodiment of FIGS. 1 through 6 as described above.

With reference to FIG. 9, the first mixing paddle 114 includes a plurality of concave vanes 342 disposed about a central rotating shaft 344 which is preferably integrally formed therewith, such as by injection molding, wherein the plurality of concave vanes 342 extend from the central rotating shaft 344 to contact a wall 346 of the housing 104. The central rotating shaft 344 is mated with the socket 134 in a manner similar to the embodiments shown in FIGS. 1 though 4 as described above. The central rotating shaft 344 defines a central rotational axis.

With further reference to FIG. 9, the central rotating shaft 344 is integrally formed to have a first gear 356 thereon, such as through injection molding or any other suitable means, such that the first annular gear 356 rotates in accordance with the handle assembly 124. The central rotating shaft 344 further includes a second end 359 juxtaposed between the plurality of concave vanes 342 and extending therefrom into the depression 112 in the housing 104 for maintaining the central rotational axis of the first mixing paddle 114 in the fixed position and stabilizing the first mixing paddle 114 during rotation.

With continued reference to FIG. 9, the lid assembly 302 further includes an attachment arm 362 disposed about the cylindrical sleeve 122 and having an aperture 363 formed therein being adapted for mounting a second mixing paddle 364 having a plurality of vanes 366 extending radially from a second rotating shaft 368 defining a second rotational axis. The second rotating shaft 368 is spaced from the central rotating shaft 344 of the first mixing paddle 314 such that the plurality of concave vanes 342 of the first mixing paddle 314 rotate around and beneath the second mixing paddle 364. The second rotating shaft 368 includes a first end 370 having an annular groove 372 therein and having a split ring 373 disposed in the groove 372 for retaining the second mixing paddle 364. The aperture 363 receives the first end 370 and secures the second mixing paddle 364 therein. The second mixing paddle 364 is integrally formed to include a second gear 376, such as though injection molding or any other suitable means. Moreover, the second gear 376 engages the first gear 356 such that when the handle assembly 124 is rotated in a first direction, thereby causing the first mixing paddle 314 to rotate in the first direction, the second mixing paddle 364 rotates in a second opposite direction while the second rotational axis remains in its fixed position.

Figure 11:
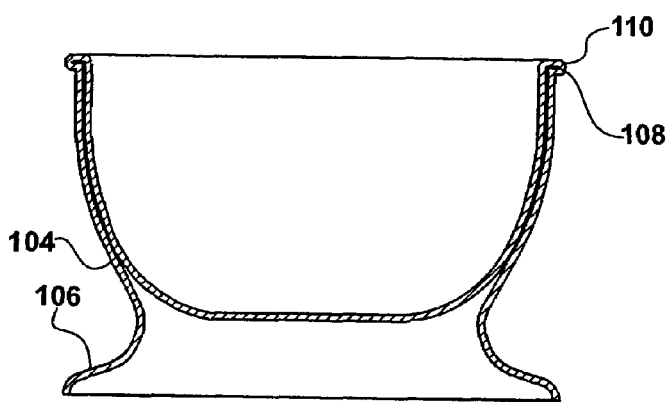
FIG. 11 is a cross-sectional view illustrating the housing.
Figure 12:
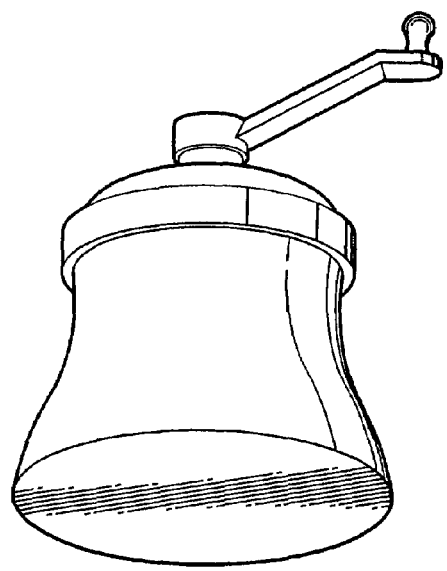
FIG. 12 is a perspective view of the mixing assembly according to another embodiment of the present invention.

Referring to FIGS. 10 and 11, a bone cement mixing bowl assembly according to another embodiment of the present invention is generally shown at 400. The mixing bowl assembly 400 includes a lid assembly 402 along with the housing 104, the rotatable handle assembly 124 and the first mixing paddle 114 shown in the embodiment of FIGS. 1 through 6 as described above.

With further reference to FIG. 10, the first mixing paddle 114 includes a plurality of concave vanes 442 disposed about a central rotating shaft 444 defining a central rotational axis wherein the plurality of concave vanes 442 extend from the central rotating shaft 444 to contact a wall 446 of the housing 104. The central rotating shaft 444 includes a first end 448 including a connector shaft 450. The shaft 450 is adapted for mating with an outer housing 435 which is further disposed in the socket 434 of the rotatable handle assembly 124 such that when the first end 448 of the central rotating shaft 444 is inserted into the socket 434 of the handle assembly 124, the shaft 450 snaps into the outer housing 435 for securing the first mixing paddle 114 to the handle assembly 124, thereby allowing the first mixing paddle 114 to rotate in accordance with the handle assembly 124 while the central rotational axis remains in a fixed position.

With further reference to FIG. 10, the outer housing 435 further includes a first gear 456 that is threaded onto a threaded portion 437 thereof such that the first gear 456 rotates in accordance with the handle assembly 124. The socket 434 is received in the sleeve 122 of lid assembly 402. The threaded portion 437 secures the first gear 456 to outer housing 435. The central rotating shaft 444 further includes a second end 459 juxtaposed between the plurality of concave vanes 442 and extending therefrom into the depression 112 in the housing 104 for maintaining the central rotational axis of the first mixing paddle 114 in the fixed position and providing stability to the first mixing paddle 114 during rotation.

As shown in FIG. 10, the lid assembly 402 further includes an attachment arm 462 disposed about the cylindrical sleeve 122 and having a channel 463 formed therein being adapted for mounting a second mixing paddle 464 having a plurality of vanes 466 extending radially from a second rotating shaft 468 defining a second rotational axis. The second rotating shaft 468 is spaced from the central rotating shaft 444 such that the plurality of concave vanes 442 of the first mixing paddle 114 rotate around and beneath the second mixing paddle 464. The second rotating shaft 468 includes a first end 470 having an annular groove 472 thereon and including a split ring 473 disposed thereon for retaining the second mixing paddle 464. The channel 463 receives ring 473 and secures the second mixing paddle 464 therein. The first end 470 of the second mixing paddle 464 further includes a threaded portion 475 integrally formed therewith. The second mixing paddle 464 further includes a second gear 476 that is threaded onto the threaded portion 475 of the first end 470. Moreover, the second gear 476 engages with the first gear 456 such that when the handle assembly 124 is rotated in a first direction, thereby causing the first mixing paddle 114 to rotate in the first direction, the second mixing paddle 464 rotates in a second opposite direction while the second rotational axis remains in its fixed position.

Figure 13:
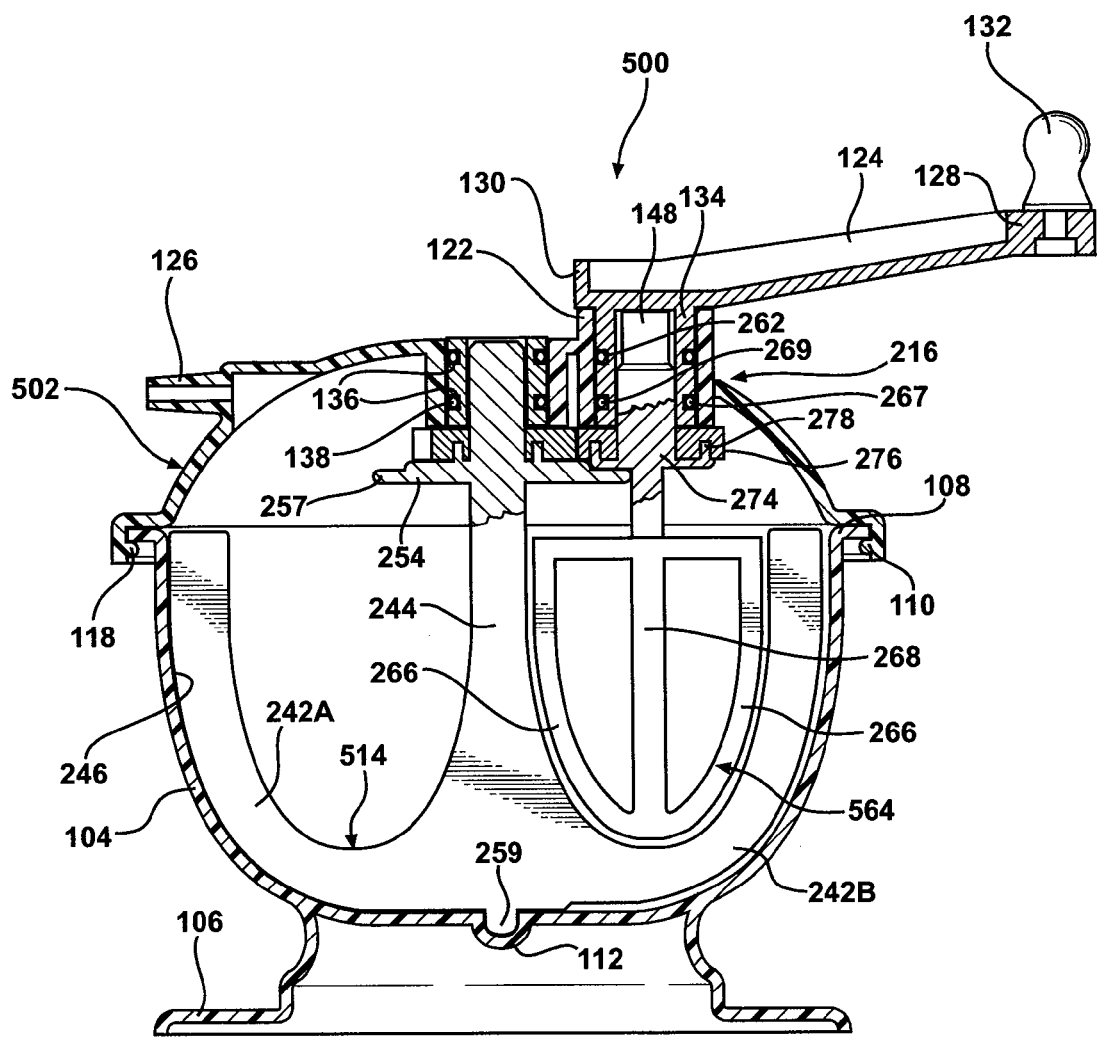
FIG. 13 is a partially cross-sectional view of the mixing assembly according to another embodiment of the present invention that illustrates, in particular, an alternative disposition for the handle.

As is clear to those skilled in the art, the handle assembly 124 and the socket 134 may be disposed on the second mixing paddle 264 rather than the first mixing paddle 214. In FIG. 13, a bone cement mixing bowl assembly 500 according to this other embodiment of the present invention is shown.

The mixing bowl assembly 500 is the same as the embodiment shown in FIGS. 7 and 8, except that the handle assembly 124 and the socket 134 are disposed on a second mixing paddle 564 rather than a first mixing paddle 514. The reference numbers have been retained as in FIGS. 7 and 8 for ease of comparison. As would be understood by one of ordinary skill in the art, the same structures are shown in FIG. 13 as FIGS. 7 and 8, the only difference being which axis the structure is placed on. The means of rotatably securing the first mixing paddle 514 and the second mixing paddle 564 to each other, to a lid assembly 502 and to the housing 104 may be in accordance with any of the embodiments shown in FIGS. 1-12 and discussed herein or any other suitable means.

An alternative embodiment of the bone cement mixing bowl assembly 600 is shown in FIGS. 14-20. In this embodiment, the mixing bowl assembly 600 includes a lid assembly 602 and a housing 604 forming a concave interior and having an open top. The housing 604 includes a base 606 for supporting the housing 604 and a rim 608 for securing the lid assembly 602 to the housing 604. The housing 604 further includes a depression 610 formed therein for stabilizing a first mixing paddle 666, described below. The housing 604 of the present invention may be formed in a variety of suitable shapes as discussed above.

Figure 14:
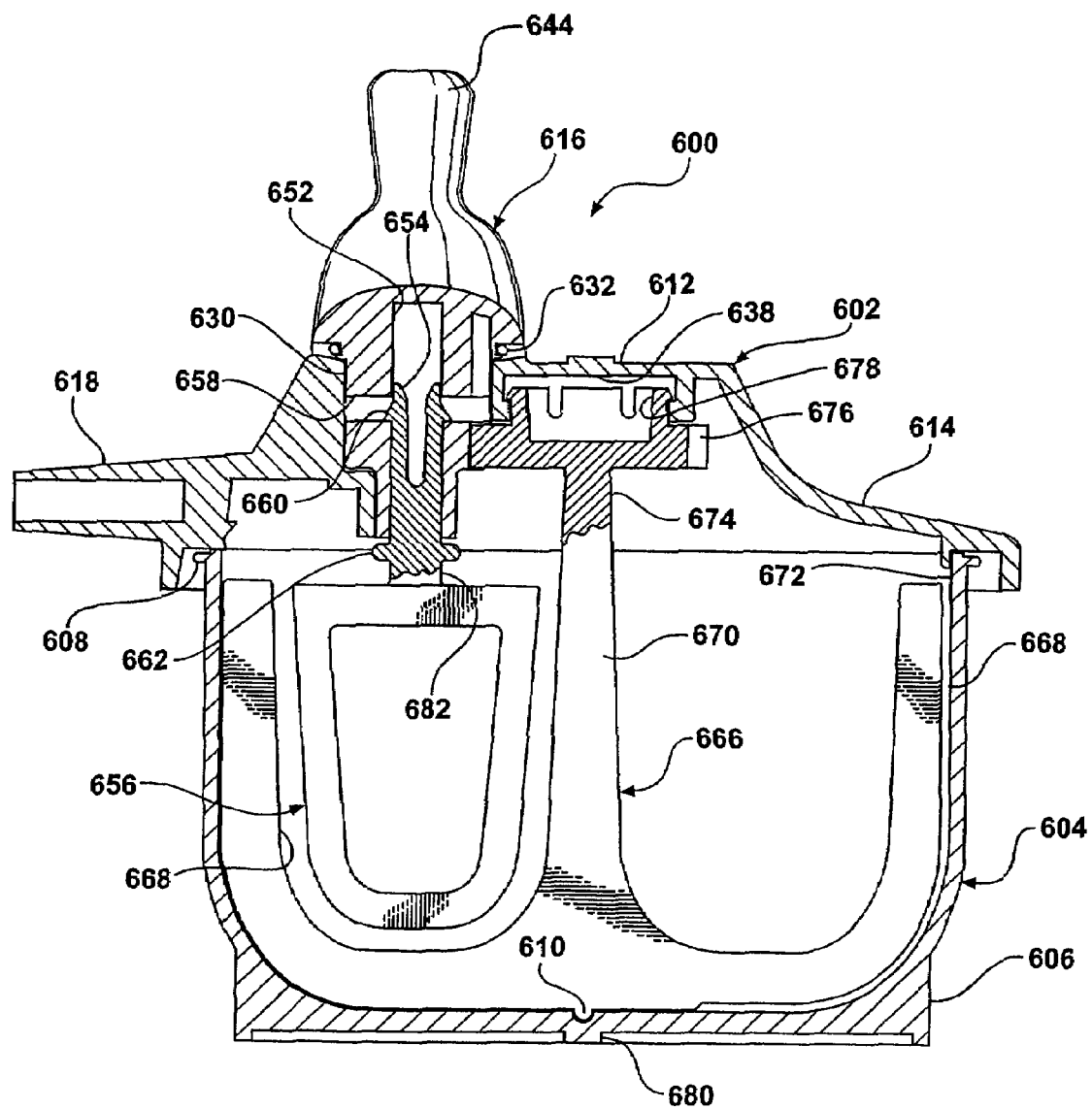
FIG. 14 is a partially cross-sectional view of the mixing assembly according to another embodiment of the present invention.
Figure 15:
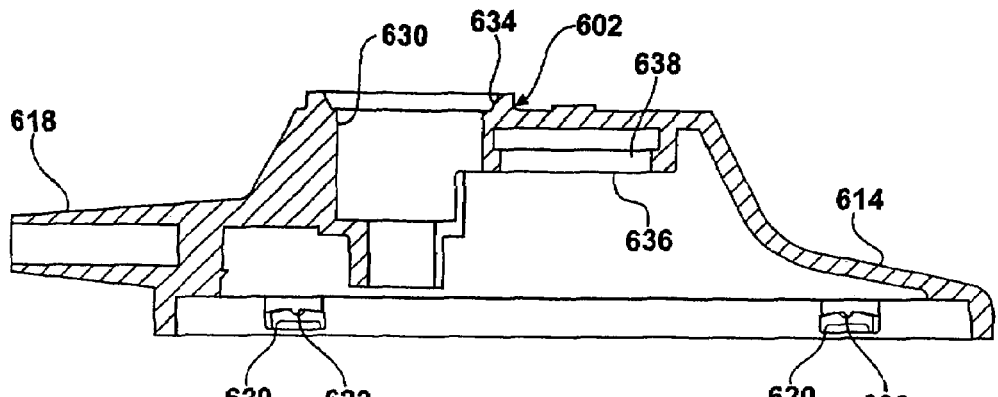
FIG. 15 is a cross-sectional view of the lid of the mixing assembly of FIG. 14.
Figure 16:
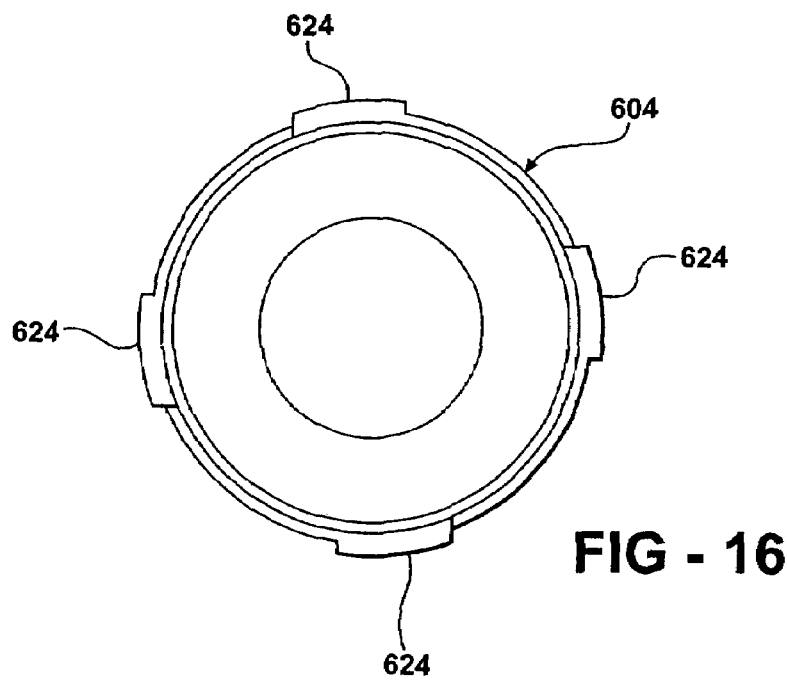
FIG. 16 is a top plan view of the housing of the mixing assembly of FIG. 14.
Figure 17:
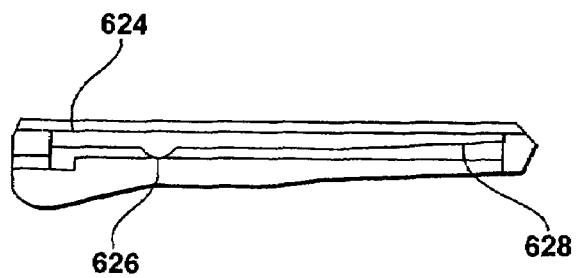
FIG. 17 is an enlarged view of a locking ramp of the mixing assembly of FIG. 14.

The mixing bowl assembly 600 further includes a rotatable handle assembly 616 and a vacuum port 618. The vacuum port 618 may further include a charcoal plug, not shown. As shown in FIGS. 15-17, the lid assembly 602 further includes a plurality of tabs 620 each of which includes a central notch 622. Alternately, the plurality of tabs 620 can include a nub instead of a central notch 622. The rim 608 includes a corresponding plurality of locking ramps 624. Each locking ramp 624 includes a locking nub 626 and a ramp 628. The lid assembly 602 is secured to the housing 604 by placing the lid assembly 602 on the rim 608 and rotating the lid assembly 602 relative to the housing 604 such that each locking nub 626 is received in a central notch 622 of its corresponding tab 620 or each nub on the plurality of tabs passes over the corresponding locking nub on the locking ramps. The rim 608 may further include a sealing member, not shown, such as a strip of volara, as is known in the art. The lid assembly 602 includes a first cylindrical sleeve 630 for mounting the rotatable handle assembly 616 onto the lid assembly 602. The first cylindrical sleeve includes a beveled rim 634 that receives a seal 632 for sealing the connection between the rotatable handle assembly 616 and the lid assembly 602, as shown in FIG. 14. The lid assembly 602 further includes a second cylindrical sleeve 636 having an inward projecting rim 638.

Figure 18:
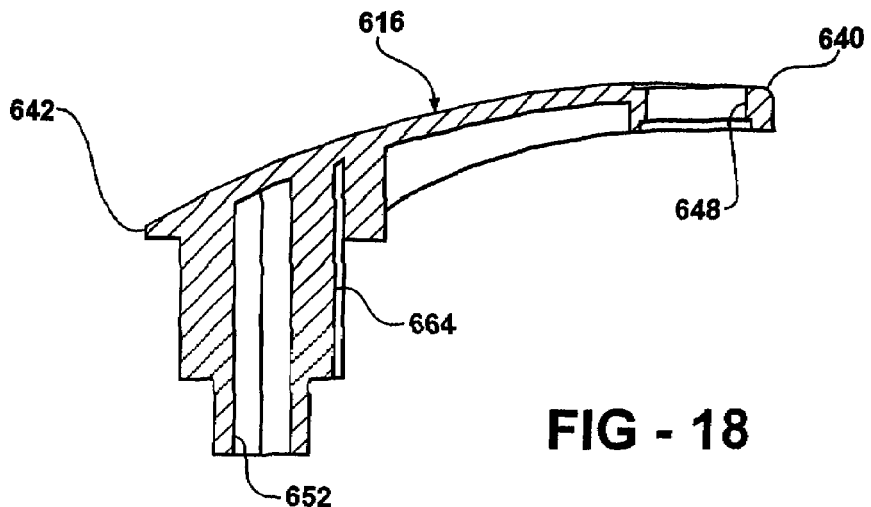
FIG. 18 is a cross-sectional view of the handle of the mixing assembly of FIG. 14.
Figure 19:
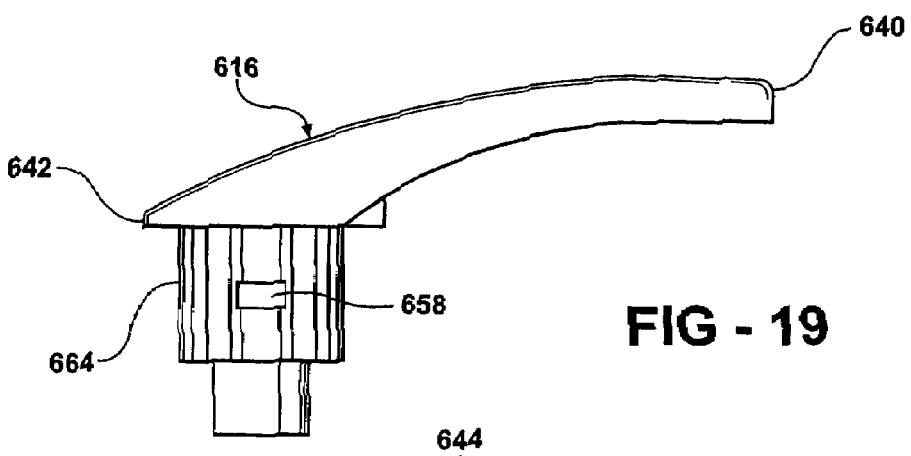
FIG. 19 is a perspective view of the handle of the mixing assembly of FIG. 14.
Figure 20:
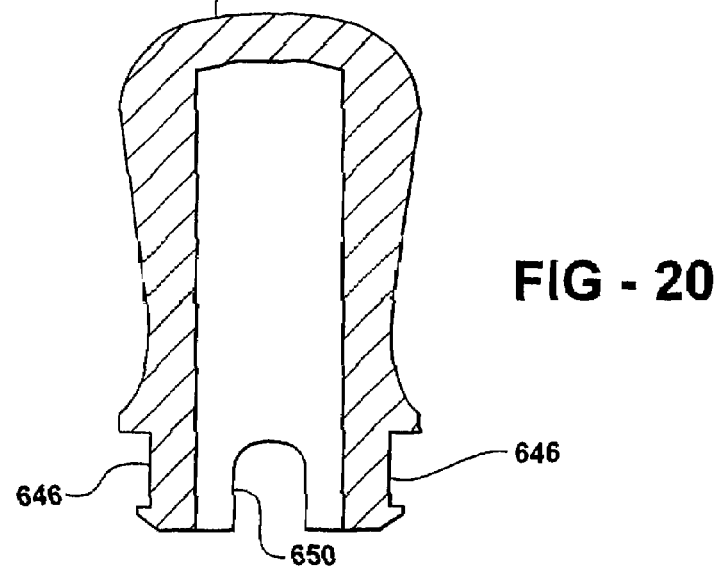
FIG. 20 is a cross-sectional view of a knob of the mixing assembly of FIG. 14.

As shown in FIGS. 18-20, the rotatable handle assembly 616 includes a grasping end 640 opposite a locking end 642. A knob 644 is received within a knob hole 648 located adjacent the grasping end 640. The knob 644 includes a plurality of knob tabs 646 separated by cut-outs 650. The knob 644 snaps into the knob hole 648. The locking end 642 of the rotatable handle assembly 616 includes a socket 652 for receiving a second mixing paddle 656, described below. The socket has a non-circular shape to enable transference of torque from rotation of the rotatable handle assembly 616 to the second mixing paddle 656. The shape of socket 652 can be square, hexagonal, or any other non-circular shape.

The second mixing paddle 656 includes a first end 654 having a shape adapted to be received in the socket 652. In the embodiment shown the first end 654 includes a plurality of tabs 660 that are received in a corresponding number of recesses 658 in the rotatable handle assembly 616, thereby positively locking the second mixing paddle 656 to the rotatable handle assembly 616. The rotatable handle assembly further includes a gear 664 for engaging a corresponding gear 676 on first mixing paddle 666, described below. The second mixing paddle 656 further includes a stop 662.

The first mixing paddle 666 comprises a central rotating shaft 670 defining a central rotational axis and has a plurality of concave vanes 668, one of which touches a wall 672 of the housing 604 and the other of which is spaced apart from the wall 672. Thus, as described above, one of the vanes 668 scrapes the bone cement off the wall 672 while the other spreads the bone cement within the housing 604. A first end 674 of the first mixing paddle 666 includes a gear 676 that engages the gear 664 of the rotatable handle assembly 616. The first end 674 further includes a plurality of tabs 678 that are received in the second cylindrical sleeve 636 and snap in place by virtue of the inward projecting rim 638, thereby securing the first mixing paddle 666 to the lid assembly 602. A second end 680 of the first mixing paddle 666 is received in the depression 610 thereby helping to maintain the position of the central rotating shaft 670. The second mixing paddle 656 includes a second rotating shaft 682 defining a second rotational axis. The lid assembly 602 further includes a cut-out 614 enabling a user to place their hand on the lid assembly 602 thereby steadying the assembly 600 while the rotatable handle assembly 616 is rotated to mix a bone cement within the housing 604. In this embodiment, as the rotatable handle assembly 616 is rotated the second mixing paddle 656 is rotated and the first mixing paddle 666 is also rotated.

Figure 21:
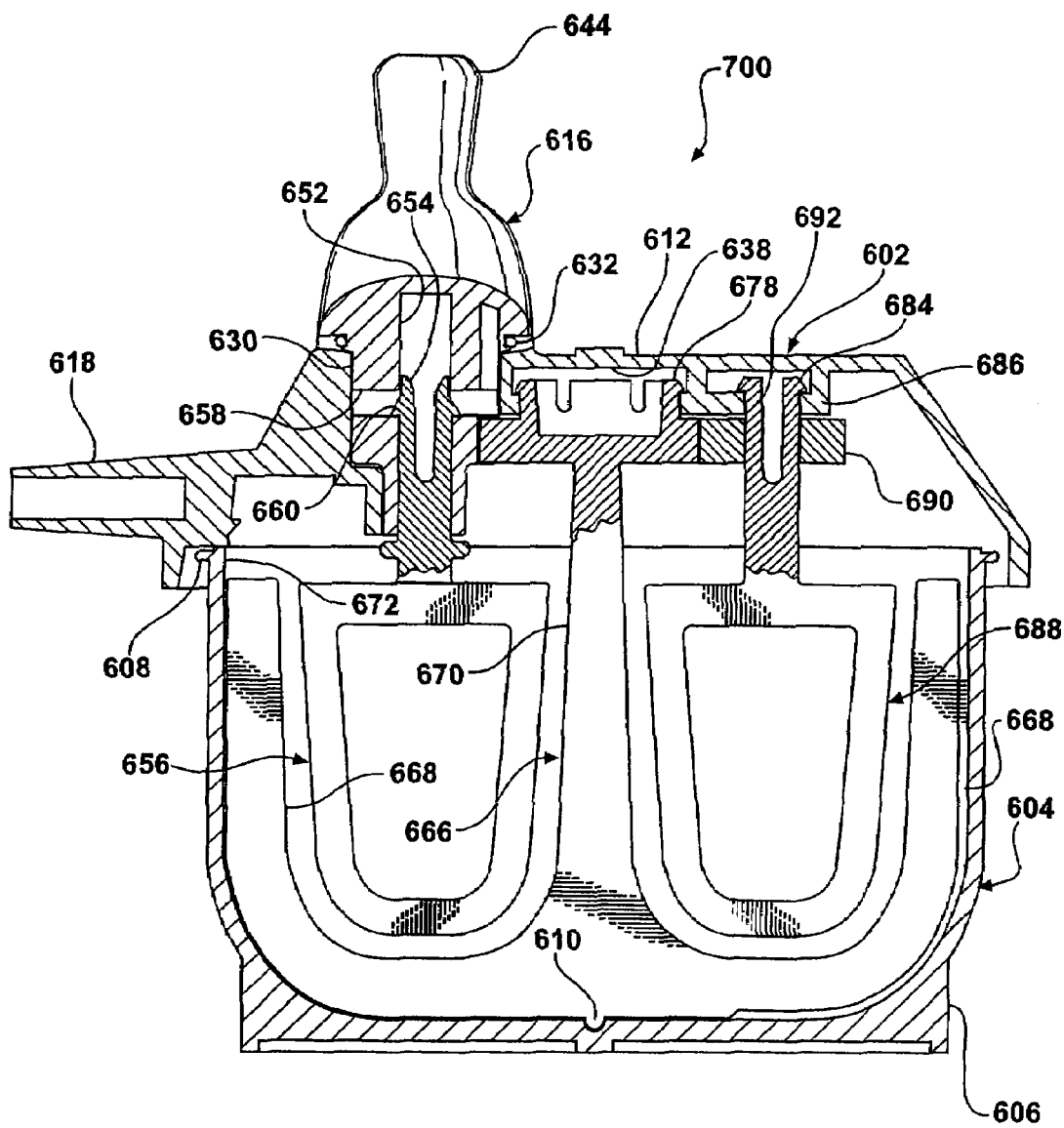
FIG. 21 is a partially cross-sectional view of the mixing assembly according to another embodiment of the present invention.
Figure 22:
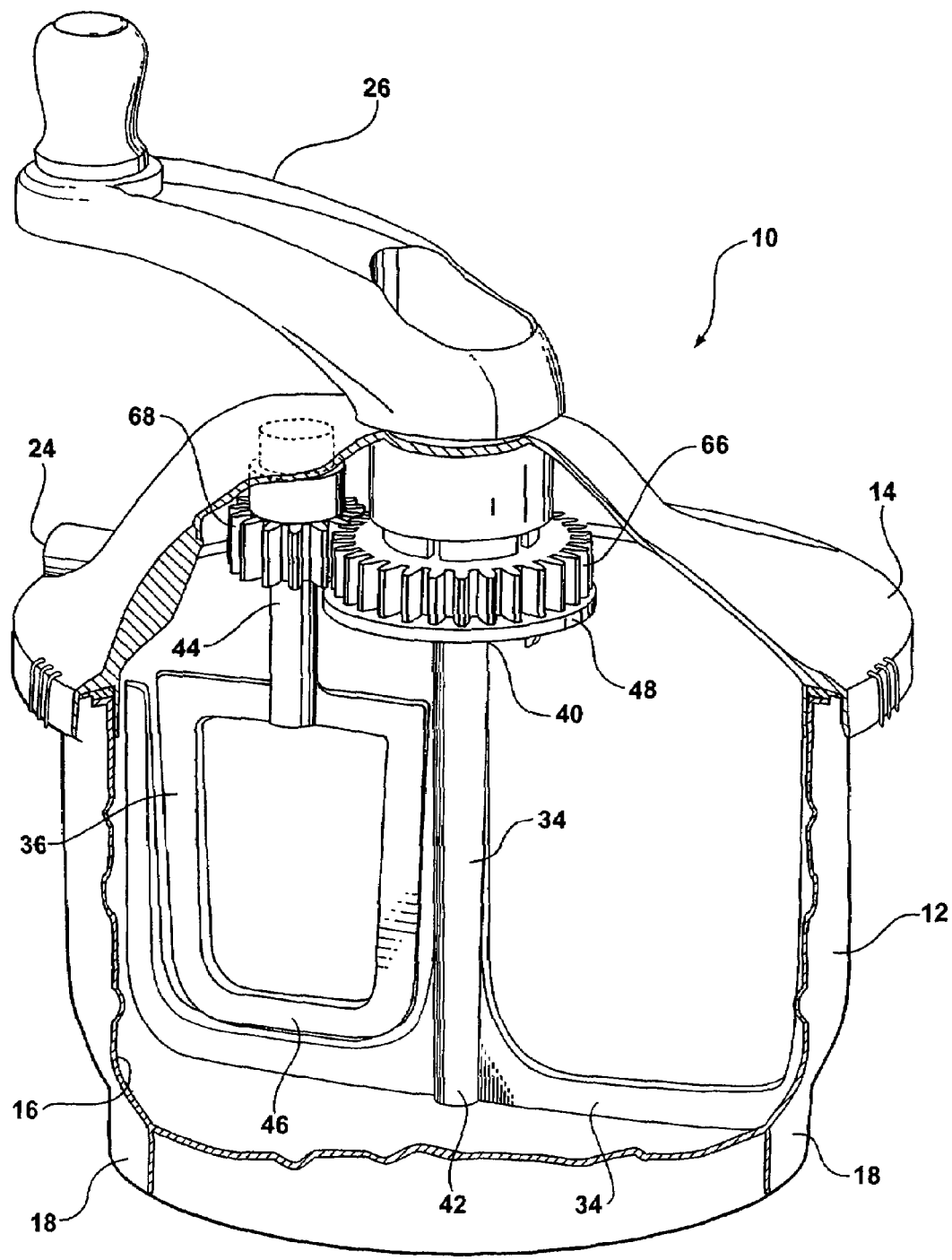
FIG. 22 is a partially cutaway perspective view of the mixing assembly according to another embodiment of the present invention.

In FIG. 21, an alternative embodiment of the bone cement mixing bowl assembly is generally shown at 700. This assembly is similar to that shown in FIGS. 14-20 with the exception that it includes at least a third mixing paddle 688. This third mixing paddle 688 is also disclosed in FIG. 42. The assembly 700 can include up to a total of four mixing paddles like second mixing paddle 656 and third mixing paddle 688. The only difference between this embodiment and that shown in FIGS. 14-20 is the addition of a third cylindrical sleeve 684 having an inward projecting rim 686. The third mixing paddle 688 includes a plurality of snap tabs 692 and a gear 690. The snap tabs 602 are received within the third cylindrical sleeve 684 and engage the inward projecting rim 686 to rotatably secure the third mixing paddle 688 to the lid assembly 602. The gear 690 engages the gear 676 of the first mixing paddle 666. Thus, rotation of the rotatable handle assembly 616 drives the first mixing paddle 666, the second mixing paddle 656, and the third mixing paddle 688. Addition of other mixing paddles would be accomplished by adding additional cylindrical sleeves with inward projecting rims to the lid assembly 602. Although not shown, assembly 700 could also be designed such that vanes 668 are shorter, and mixing paddles 656, 688 are wider such that the mixing paddles 656 and 688 scrape against wall 672.

The present invention has been described in an illustrative manner. Obviously, many modifications and variations of the present invention are possible in light of the above teachings. It is to be understood that the terminology that has been used is intended to be in the nature of words of description rather than of limitation.

What is claimed is:

1. A method of mixing bone cement, said method including the steps of:
    placing components forming the bone cement in a housing, the housing being part of a mixer that includes first and second paddles disposed in the housing that are spaced apart from each other, the first paddle having a shaft from which first and second vanes extend, the first vane shaped to have an outer edge in close proximity with an interior wall of the housing and the second vane shaped to have an outer edge spaced from the housing interior wall, the second paddle having a shaft and a vane positioned between the second paddle shaft and the first paddle vanes and positioned to rotate towards and away from the first paddle shaft;
    simultaneously rotating both the first and second paddles so that, simultaneously:
        the rotation of the first paddle first vane scrapes the bone cement under formation from the housing interior wall;
        the rotation of the first paddle second vane smears the bone cement under formation around the housing interior wall; and
        the rotation of the second paddle vane towards and away from the first paddle shaft pushes the bone cement under formation towards and then away from the first paddle shaft.

2. The method of mixing bone cement of claim 1, wherein:
    each first paddle vane has an inner edge that is located inwardly from the outer edge of the first paddle vane and spaced outwardly away from the first paddle shaft;
    the second paddle is further shaped so that the second paddle vane is located between the first paddle shaft and the inner edges of the first paddle vanes; and
    during said simultaneous rotation of the paddles, the second paddle is further rotated so that the second paddle vane rotates towards and away from the inner edges of the first paddle vanes to push the bone cement under formation around the first paddle vanes.

3. The method of mixing bone cement of claim 1, wherein:
    each first paddle vane has an inner edge that is located inwardly from the outer edge of the first paddle vane and spaced outwardly away from the first paddle shaft;
    the second paddle is further shaped so that the second paddle vane is located between the first paddle shaft and the inner edges of the first paddle vanes; and
    the paddles are further arranged so that, during said simultaneous rotation of the paddles, there is at least one instance in which the first paddle vanes and the second paddle vane are coplanar.

4. The method of mixing bone cement of claim 1, wherein:
    each first paddle vane has an inner edge that is located inwardly from the outer edge of the first paddle vane and spaced outwardly away from the first paddle shaft;
    the second paddle is further shaped to have a first vane and a second vane, both second paddle vanes being located radially outward from the second paddle shaft and inwardly of the inner edges of the first paddle vanes; and during said simultaneous rotation of the paddles, the first of the second paddle vanes pushes bone cement under formation towards or away from the first paddle shaft while, simultaneously therewith, the second of the second paddle vanes rotates towards and away from one of the first paddle vanes so as to push bone cement under formation around the one of the first paddle vanes.

5. The method of mixing bone cement of claim 1, wherein:

each first paddle vane has an inner edge that is located inwardly from the outer edge of the first paddle vane and spaced outwardly away from the first paddle shaft;

the second paddle is further shaped to have a first vane and a second vane, both second paddle vanes being located radially outward from the second paddle shaft and inwardly of the inner edges of the first paddle vanes;

during said simultaneous rotation of the paddles, the first of the second paddle vanes pushes bone cement under formation towards or away from the first paddle shaft while, simultaneously therewith, the second of the second paddle vanes rotates towards and away from one of the first paddle vanes so as to push bone cement under formation around the one of the first paddle vanes; and the paddles are further arranged so that, during said simultaneous rotation of the paddles, there is at least one instance in which the first paddle vanes and the second paddle vanes are coplanar.

6. The method of mixing bone cement of claim 1, wherein:

the housing has a bottom;

at least the first paddle first vane has a bottom section that, during said simultaneous rotation of the paddles, scrapes bone cement under formation from off the housing bottom; and the second paddle vane is shaped to have a bottom section that is located above the first paddle first vane bottom section that, during said simultaneous rotation of the paddles, crosses over the first paddle first vane bottom section to push bone cement under formation off the first paddle first vane bottom section.

7. The method of mixing bone cement of claim 1, wherein, during said simultaneous rotation of the paddles, the paddles are rotated in opposed directions.

8. The method of mixing bone cement of claim 1, wherein, during said simultaneous rotation of the paddles, the paddles are rotated so that the second paddle rotates at 2 times the rotational rate of the first paddle.

9. A method of mixing bone cement, said method including the steps of:

placing bone cement forming components in a housing, the housing having an interior wall that defines an interior space;

rotating a first paddle in the housing interior space, the first paddle having a shaft from which first and second vanes extend radially outwardly, the first vane having an outer edge positioned close to the housing interior wall so that, as the first paddle is rotated, the first vane scrapes the bone cement under formation from the housing interior wall, the second vane having an outer edge positioned away from the housing interior wall so that as the first paddle is rotated, the second vane smears the bone cement under formation around the housing interior wall and each vane has an inner edge located inward of the outer edge and that is radially spaced away from the first paddle shaft so as to define a space between the first paddle shaft and the vane; and simultaneously with the rotation of the first paddle, rotating a second paddle in the housing interior space, the second paddle having a shaft that is spaced radially from the first paddle shaft and a vane that is spaced radially from the second paddle shaft, the second paddle positioned so as to rotate within the space between the first paddle shaft and the first paddle vanes, the second paddle further shaped so that, as the second paddle rotates, the second paddle vane initially rotates towards and away from the first paddle shaft to push bone cement under formation towards and away from the first paddle shaft and then rotates towards and away from one of the first paddle vanes to push bone cement under formation around the one of the first paddle vanes.

10. The method of mixing bone cement of claim 9, wherein:

the second paddle is further shaped to have first and second vanes, each second paddle vane having an outer edge that is located radially away from the second paddle shaft; and during said simultaneous rotation of the paddles, the second paddle is rotated so that, as the first of the second paddle vanes pushes the bone cement under formation towards or away from the first paddle shaft, the second of the second paddle vanes pushes the bone cement under formation around one of the first paddle vanes.

11. The method of mixing bone cement of claim 9, wherein:

the second paddle is further shaped to have a first vane and a second vane, both second paddle vanes being located radially outward from the second paddle shaft and inwardly of the inner edges of the first paddle vanes; and the paddles are further arranged so that, during said simultaneous rotation of the paddles, there is at least one instance in which the first paddle vanes and the second paddle vanes are coplanar.

12. The method of mixing bone cement of claim 9, wherein:

the housing interior wall has a base section that defines a bottom of the housing interior space;

at least the first paddle first vane is shaped to have a base section positioned to abut the housing interior wall base section so that, during said simultaneous rotation of the paddles, the first paddle first vane base section scrapes bone cement forming material from the base section of the housing interior wall; and the second paddle is shaped so as to have: first and second vanes that are spaced apart, both second paddle vanes being located between the first paddle shaft and the inner edges of the first paddle vanes; and a cross beam that connects the second paddle vanes, the cross beam being located above space occupied by the first paddle first vane base section, so that during said simultaneous rotation of the paddles:

the first of the second paddle vanes pushes bone cement under formation towards or away from the first paddle shaft;

the second of the second paddle vanes pushes bone cement under formation around the first paddle first vane; and the second paddle cross beam pushes the bone cement under formation off the first paddle first vane base section.

13. The method of mixing bone cement of claim 9, wherein, during said simultaneous rotation of the paddles, the paddles are rotated so that the second paddle rotates at 2 times the rotational rate of the first paddle.

14. The method of mixing bone cement of claim 9, wherein:

the housing interior wall has a base section that defines a bottom of the housing interior space;

at least the first paddle first vane is shaped to have a base section positioned to abut the housing interior wall base section so that, during said simultaneous rotation of the paddles, the first paddle first vane base section scrapes bone cement forming material from the housing interior wall base section; and the second paddle vane is shaped to have:

a vertical section that, during said simultaneous rotation of the paddles, is the portion of the second paddle vane that pushes bone cement under formation towards and away from the first paddle shaft and around the first paddle vanes; and a horizontal section that extends from the vertical section so that, during said simultaneous rotation of the paddles, the second paddle vane horizontal section crosses above the first paddle first vane base section to push bone cement under formation off the first paddle first vane base section.

15. The method of mixing bone cement of claim 14, wherein:

both paddles are rotatably mounted to a lid that is disposed over the housing and both paddles are able to move longitudinally relative to the lid; and after said step of placing the bone cement forming components in the housing, the lid, including the paddles, is placed over the housing so as to position the paddles in the housing interior space wherein during said step of placing the lid over the housing:

the first paddle is positioned so that the first paddle first vane abuts the housing interior wall; and the second paddle is positioned so that the second paddle vane is spaced away from the first paddle first vane.

16. A method of mixing bone cement, said method including the steps of:

placing bone cement forming components in a housing, the housing having an interior wall that defines an interior space, the housing interior wall having a base section that defines a bottom of the housing interior space and a side section located above the base section that defines sides of the housing interior space wherein the bone cement-forming components are placed in the housing interior space;

rotating a first paddle in the housing interior space, the first paddle having a shaft with an end disposed in the housing and first and second vanes that extend radially away from the end of the shaft, both vanes having an outer edge that extends from the shaft above the base section of the housing interior wall and upwardly along the side section of the interior wall and an inner edge located inward of the outer edge so as to define a space between the vane and the shaft, the first vane outer edge located close to the housing interior wall so that, as the first paddle is rotated, the first vane scrapes bone cement under formation from both the base section and side section of the housing interior wall, the second vane outer edge positioned away from the housing interior wall so that as the first paddle is rotated, the second vane smears the bone cement under formation around the housing interior wall; and simultaneously with said rotation of the first paddle, rotating a second paddle in the housing interior space, the second paddle having a shaft that is radially offset from the first paddle shaft and at least one vane that is connected to and radially offset from the second paddle shaft, the second paddle vane shaped and positioned so that, as the second paddle is rotated, the second paddle vane rotates between the first paddle shaft and the first paddle vanes and, during said rotation:

rotates towards and away from the first paddle shaft to push bone cement under formation towards and away from the first paddle shaft; and crosses over the first paddle first vane to push bone cement under formation off a portion of the first paddle first vane that scrapes bone cement under formation off the base section of the housing interior wall.

17. The method of mixing bone cement of claim 16, wherein the second paddle vane is shaped to have:

an upper section that extends from the second paddle shaft that is shaped relative to the second paddle shaft so that, during said simultaneous rotation of the paddles, the second paddle vane upper section first rotates towards and away from the first paddle shaft to push bone cement under formation towards and away from the first paddle shaft and then towards and away from the first paddle first vane to push bone cement under formation around a section of the first paddle first vane that scrapes bone cement under formation off the side section of the housing interior wall; and a lower section that extends from the upper section that is located above a section of the first paddle first vane that scrapes the bone cement under formation off the base section of the housing interior wall, the second paddle vane upper section positioned so that, during said simultaneous rotation of the paddles, the second paddle vane lower section crosses over the section of the first paddle first vane that scrapes bone cement under formation off the base section of the housing interior wall to push the bone cement under formation off the first paddle first vane section.

18. The method of mixing bone cement of claim 16, wherein the second paddle is shaped to have:

a first vane that extends vertically, that is connected to and located radially away from the second paddle shaft;

a crossbeam that extends horizontally from the second paddle first vane that is located above a section of the first paddle first vane that scrapes the bone cement under formation off the base section of the housing interior wall, the crossbeam positioned so that, during said simultaneous rotation of the paddles, the crossbeam crosses over the section of the first paddle first vane that scrapes bone cement under formation off the base section of the housing interior wall so as to push the bone cement under formation off the first paddle first vane section; and a second vane that extends vertically, the second paddle first and second vanes being positioned so that as one of the second paddle vanes pushes bone cement under formation towards or away from the first paddle shaft, the other of the second paddle vanes pushes the bone cement under formation from the first paddle first vane.

19. The method of mixing bone cement of claim 16, wherein the paddles are shaped and are arranged, so that, during said simultaneous rotation of the paddles, there is at least one instance in which the first paddle vanes and the second paddle vane are coplanar.

20. The method of mixing bone cement of claim 16, wherein:

both paddles are rotatably mounted to a lid that is disposed over the housing and both paddles are able to move longitudinally relative to the lid; and after said step of placing the bone cement forming component in the housing, the lid, including the paddles is placed over the housing so as to position the paddles in the housing interior space wherein during said step of placing the lid over the housing:

the first paddle is positioned so that the first paddle first vane abuts the housing interior wall; and the second paddle is positioned so that the second paddle vane is spaced away from the first paddle first vane.

* * * * *

UNITED STATES PATENT AND TRADEMARK OFFICE
CERTIFICATE OF CORRECTION

PATENT NO. : 7,645,066 B2　　　　　　　　　　　　　　　　　　　　　　　Page 1 of 1
APPLICATION NO. : 11/301177
DATED : January 12, 2010
INVENTOR(S) : Tague et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 723 days.

Signed and Sealed this

Sixteenth Day of November, 2010

David J. Kappos
*Director of the United States Patent and Trademark Office*